United States Patent [19]

Clough et al.

[11] Patent Number: 5,021,581

[45] Date of Patent: Jun. 4, 1991

[54] FUNGICIDES

[75] Inventors: John M. Clough, Marlow; Christopher R. A. Godfrey, Bracknell; Paul J. de Fraine, Wokingham; Michael G. Hutchings, Prestwich; Vivienne M. Anthony, Maidenhead, all of England

[73] Assignee: Imperial Chemical Industries PLC, London, England

[21] Appl. No.: 151,522

[22] Filed: Feb. 2, 1988

[30] Foreign Application Priority Data

Feb. 9, 1987 [GB] United Kingdom ................ 8702845
May 5, 1987 [GB] United Kingdom ................ 8710594

[51] Int. Cl.$^5$ .......................................... C07D 211/72
[52] U.S. Cl. .................................... 546/309; 544/298; 544/305; 544/315; 544/318; 544/329; 560/60
[58] Field of Search .......................... 560/60; 546/309; 544/298, 303, 315, 318, 329; 514/352, 256

[56] References Cited

FOREIGN PATENT DOCUMENTS 0226917 12/1986 European Pat. Off. .
0178826 4/1988 European Pat. Off. .
2172595 9/1986 United Kingdom .

OTHER PUBLICATIONS

Chemical Abstracts, vol. 107(21) No. 190037s.

Primary Examiner—Paul J. Killos
Attorney, Agent, or Firm—Cushman, Darby & Cushman

[57] ABSTRACT

Fungicidal compounds of the formula (I):

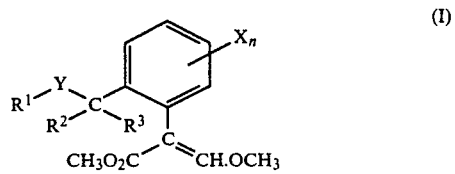

and stereoisomers thereof, wherein $R^1$ is optionally substituted aryl or optionally substituted heteroaryl; Y is oxygen, sulphur or $NR^4$; $R^2$, $R^3$ and $R^4$, which may be the same or different, are hydrogen, $C_{1-4}$ alkyl or $C_{2-4}$ alkenyl; X is halogen, $C_{1-4}$ alkyl, $C_{2-4}$ alkenyl, $C_{1-4}$ alkoxy, nitro or cyano; and n is 0 or an integer of 1 to 4; provided that when Y is oxygen, n is O and $R^1$ is unsubstituted phenyl at least one of $R^2$ and $R^3$ is other than hydrogen or methyl.

9 Claims, No Drawings

FUNGICIDES

This invention relates to derivatives of propenoic acid useful as fungicides, to processes for preparing them, to fungicidal compositions containing them, and to methods of using them to combat fungi, especially fungal infections in plants.

The invention provides a compound having the formula (I):

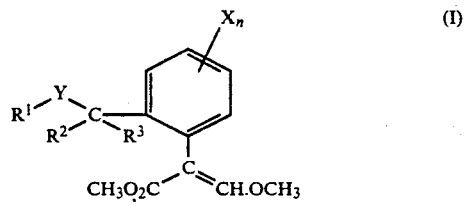

and stereoisomers thereof, wherein $R^1$ is optionally substituted aryl or optionally substituted heteroaryl; Y is oxygen, sulphur or $NR^4$; $R^2$, $R^3$ and $R^4$, which may be the same or different, are hydrogen, $C_{1-4}$ alkyl or $C_{2-4}$ alkenyl; X is halogen (fluorine, chlorine, bromine or iodine), $C_{1-4}$ alkyl, $C_{2-4}$ alkenyl, $C_{1-4}$ alkoxy, nitro or cyano; and n is 0 or an integer of 1 to 4; provided that when Y is oxygen, n is 0 and $R^1$ is unsubstituted phenyl at least one of $R^2$ and $R^3$ is other than hydrogen or methyl.

In one aspect the invention provides compounds of the formula (I) as defined above in which Y is oxygen.

In another aspect the invention provides compounds of the formula (I) as defined above in which $R^1$ is optionally substituted hereroaryl.

In still another aspect the invention provides compounds of the formula (I) as defined above in which $R^1$ is optionally substituted aryl and Y is $NR^4$.

In yet another aspect the invention provides compounds of the formula (I) as defined above in which $R^1$ is optionally substituted aryl, Y is oxygen or sulphur but $R^2$ and $R^3$ are not both hydrogen.

In yet another aspect the invention provides compounds of the formula (I) as defined above in which X is $C_{2-4}$ alkenyl.

The compounds of the invention contain at least one carbon-carbon double bond, and are sometimes obtained in the form of mixtures of geometric isomers. However, these mixtures can be separated into individual isomers, and this invention embraces such isomers, and mixtures thereof in all proportions including those which consist substantially of the (Z)-isomer and those which consist substantially of the (E)-isomer.

The individual isomers which result from the unsymmetrically substituted double bond of the propenoate group are identified by the commonly used terms "(E)" and "(Z)". These terms are defined according to the Cahn-Ingold-Prelog system which is fully described in the literature (see, for example, J. March, "Advanced Organic Chemistry", 3rd edition, Wiley-Interscience, page 109 et seq).

Usually one isomer is more active fungicidally than the other, the more active isomer usually being the one wherein the groups —$CO_2CH_3$ and —$OCH_3$ are on opposite sides of the olefinic bond of the propenoate group (the (E)-isomer). These (E)-isomers form a preferred embodiment of the invention.

The substituent $R^1$ in compound (I) is optionally substituted aryl or optionally substituted heteroaryl. The term "aryl" includes phenyl in particular, and naphthyl. The term "heteroaryl" includes 5- and 6-membered heterocyclic groups containing one or more of each of the heteroatoms O, S and N (preferably S or N), and fused benzenoid and heteroaromatic ring systems. Examples of heteroaryl groups which $R^1$ may be are pyridinyl, pyrimidinyl, pyrazinyl, pyridazinyl, 1,2,3-, 1,2,4-, and 1,3,5-triazinyl, 1,2,4,5-tetrazinyl, thienyl, quinolinyl, isoquinolinyl, quinoxalinyl and benzothienyl.

Substituents which may be present in the optionally substituted aryl and heteroaryl moieties include one or more of the following; halogen, hydroxy, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl, trichloromethyl, and chloro- and bromomethyl), halo($C_{1-4}$)alkoxy (especially trifluoromethoxy), $C_{1-4}$ alkylthio (especially methylthio), hydroxy($C_{1-4}$)alkyl (especially hydroxymethyl), ($C_{1-4}$)alkoxy($C_{1-4}$)alkyl, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridinyl or pyrimidinyl), optionally substituted aryloxy (especially optionally substituted phenoxy), optionally substituted heteroaryloxy (especially optionally substituted pyridinyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridinyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridinylethenyl or pyrimidinylethenyl), optionally substituted aryl($C_{1-4}$)alkoxy (especially optionally substituted benzyloxy), optionally substituted heteroaryl($C_{1-4}$)alkoxy (especially optionally substituted pyridinyl- or pyrimidinyl($C_{1-4}$)alkoxy), optionally substituted aryloxy ($C_{1-4}$)alkyl (especially optionally substituted phenyloxymethyl), optionally substituted heteroaryloxy($C_{1-4}$)alkyl (especially optionally substituted pyridinyl- or pyrimidinyloxy($C_{1-4}$-)alkyl), acyloxy (especially acetyloxy and benzoyloxy), cyano, thiocyanato, nitro, —NR'R", —NHCOR', —NHCONR'R", —CONR'R", —COOR', —$OSO_2R'$, —$SO_2R'$, —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, optionally substituted aryl (especially optionally substituted phenyl) or optionally substituted aryl($C_{1-4}$)alkyl (especially optionally substituted benzyl). Substituents which may be present in the optionally substituted aryl and heteroaryl moieties include one or more of those aryl and heteroaryl substituents described immediately above.

Therefore, in yet another aspect, the invention provides compounds of the formula (I) as defined above in which $R^1$ is aryl optionally substituted with one or more of hydroxy, $C_{3-6}$ cycloalkyl($C_{1-4}$)alkyl, aryl($C_{1-4}$)alkoxy, aryloxy($C_{1-4}$)alkyl, acyloxy, CR=NR" or N=CR'R" and R' and R" are independently hydrogen, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

In yet another aspect the invention provides compounds of the formula (I) as defined above in which $R^1$ is aryl optionally substituted with one or more of NR'R", NHCOR', NHCONR'R", CONR'R", $CO_2R'$, $OSO_2R'$, $SO_2R'$ or COR', R' is $C_{3-6}$ cycloalkyl($C_{1-4}$)alkyl or benzyl and R" is hydrogen, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

In yet another aspect the invention provides the (E)-isomers of the compounds of the formula (Ia):

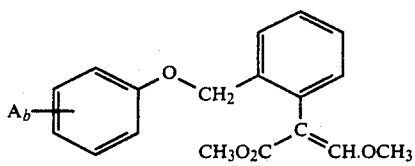

(Ia)

in which $A_b$ is selected from the group comprising 2-bromo; 3-iodo; 2-ethyl; 3-iso-propyl; 3-t-butyl; 3-trifluoromethoxy; 3-amino; 4-phenyl; 2-carboxy; 3-methoxycarbonyl; 2-hydroxy; 2,3-difluoro; 3,5-difluoro; 2,3-dimethoxy; 2-fluoro-4-chloro; 2-chloro-5-fluoro; 2-fluoro-6-methyl; 3-methyl-4-fluoro; 3-fluoro-5-methoxy; 2-methoxy-3-fluoro; 2-chloro-4-methyl; 2-methyl-5-chloro; 2-chloro-6-methoxy; 3-methoxy-4-chloro; 3-methyl-5-methoxy; 2,4,5-trifluoro; 2,4,6-trichloro; 2,4,6-trimethyl; 2,6-difluoro-4-chloro; 2,6-dimethyl-4-fluoro; 2,3,5,6-tetrachloro; pentafluoro; and pentachloro.

Where substituents in the aryl or heteroaryl moieties are in adjacent positions they may join to form a fused ring, either aromatic or aliphatic, optionally containing one or more hetero atoms. Examples of $R^1$ where substituents join to form fused rings are dibenzo-p-dioxinyl, thianthrenyl, phenoxathiinyl, dibenzofuranyl and dibenzothienyl.

When Y is oxygen and $R^1$ is phenyl it is preferred that the phenyl ring is substituted. When Y is $NR^4$ it is preferred that $R^1$ is substituted to reduce the basicity of the $NR^4$ nitrogen atom. This may be achieved by using as a substituent an electron withdrawing group.

When any of the substituents $R^2$, $R^3$, $R^4$ and X are $C_{1-4}$ alkyl, or $C_{1-4}$ alkoxy, the alkyl moiety can be in the form of straight or branched chains, that is, the moiety may be methyl, ethyl, n- or iso-propyl, or n-, sec-, iso- or t-butyl. Other references herein to $C_{1-4}$ alkyl and $C_{1-4}$ alkoxy carry the same meaning.

When any of the substituents $R^2$, $R^3$, $R^4$ and X are $C_{2-4}$ alkenyl, these groups can be in the form of straight or branched chains and, where appropriate, may have either the (E)- or the (Z)-configuration. Examples of such groups are vinyl, allyl, —C—($CH_3$):$CH_2$, and (E)- and (Z)-crotyl. Other references herein to $C_{2-4}$ alkenyl carry the same meaning.

It is preferred that $R^2$ and $R^3$ are both hydrogen and that $R^4$ is hydrogen or methyl.

When n is 2 or more, the substituents X may be the same or different. It is generally preferred, however, that n is 0 or 1.

In yet another aspect the invention provides compounds of the formula (Ib):

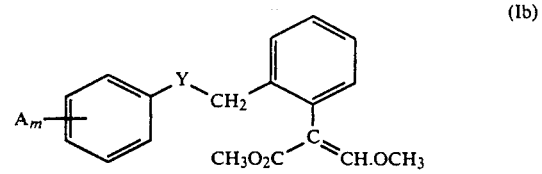

(Ib)

especially the (E)-isomer, in which Y has the meaning given before; m is an integer of 1 to 5; and A is halo (especially fluoro or chloro), hydroxy, $C_{1-4}$ alkyl (especially methyl or ethyl), halo($C_{1-4}$)alkyl (especially halomethyl, particularly trifluoromethyl, difluoromethyl, fluoromethyl or trichloromethyl), $C_{1-4}$ alkoxy (especially methoxy), halo($C_{1-4}$)alkoxy (especially trifluoromethoxy), phenyl, phenoxy, nitro, amino, acylamino (especially formamido and acetylamino), cyano, carboxy, $C_{1-4}$ alkoxycarbonyl (especially methoxycarbonyl) or $C_{1-4}$ alkylcarbonyloxy (especially acetoxy).

When m is 2 or more it is preferred that the substituents A, which may be the same or different, are fluoro, chloro, bromo, hydroxy, methyl, trifluoromethyl, difluoromethyl, fluoromethyl, trichloromethyl, methoxy, nitro, cyano, methoxycarbonyl or methylcarbonyloxy. Examples of combinations of the substituents $A_m$ when m is 2 or more are difluoro, dichloro, dimethyl, dimethoxy, fluoro-chloro, fluoro-methyl, fluoro-methoxy, chloromethyl, chloro-methoxy, methyl-methoxy, trifluoro, trichloro, trimethyl, difluoro-chloro, dimethyl-fluoro, tetrachloro and pentafluoro.

In another aspect the invention provides compounds of the formula:

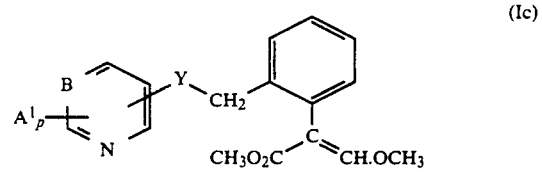

(Ic)

especially the (E)-isomer, in which B is N or CH; Y has the meaning given before; p is O or an integer of 1 to 3 when B is N, or O or an integer of 1 to 4 when B is CH; and $A^1$ has the meaning ascribed to A above.

Compounds are preferred in which the basicity of the nitrogen atom(s) of the heterocyclic ring is reduced. Accordingly it is preferred that Y is attached to a position ortho to a ring nitrogen atom, or a substituent $A^1$ (especially methoxy) is attached to a position ortho to a ring nitrogen atom, or both.

When p is 2 or more, preferred values of $A^1$ are those preferred values ascribed to A when m is 2 or more. Examples of combinations of the substituents $A^1_p$ when p is 2 or more are difluoro, dichloro, dibromo, chlorofluoro, dichloro-fluoro, bromo-fluoro, bromo-chloro, fluoro-trifluoromethyl, chloro-trifluoromethyl, dichloro-trifluoromethyl, bromo-trifluoromethyl, fluorocyano, chloro-cyano, bromo-cyano, dicyano, cyano-trifluoro, chloro-hydroxy, bromo-hydroxy, chloromethoxy, bromo-methoxy, chloro-nitro, cyano-nitro, methoxy-nitro, nitro-trifluoromethyl, chloro-acetyloxy, trifluoro, and when B is CH, cyano-trifluoro and tetrafluoro.

In another particular aspect, the invention provides the (E)-isomers of the compounds of the formula (Id):

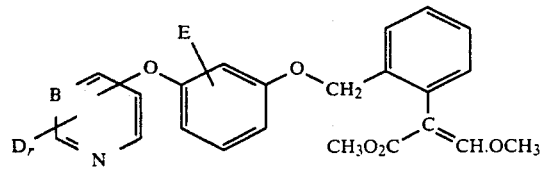

(Id)

in which q is 0 or an integer of 1 to 5; D is halo, hydroxy, $C_{1-4}$ alkyl, halo($C_{1-4}$)alkyl, $C_{1-4}$ alkoxy, halo($C_{1-4}$)alkoxy or phenoxy; and E is hydrogen or halogen.

In another particular aspect, the invention provides the (E)-isomers of the compounds of the formula (Ie):

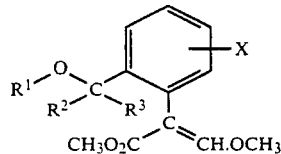

(Ie)

in which B is N or CH; r is 0 or an integer of 1 to 3 when B is N or 0 or an integer of 1 to 4 when B is CH and D and E are as defined above.

In yet another particular aspect, the invention provides the (E)-isomers of the compounds of the formula (If):

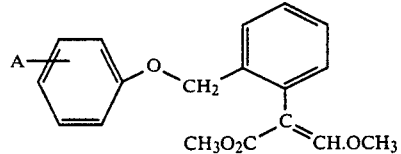

(If)

in which A is 3-bromo, 3-chloro or 4-chloro.

The invention is illustrated by the components listed in Table I which follows.

TABLE I

| COMPOUND No. | $R^1$ | X | $R^2$ | $R^3$ | Isomer* | Olefinic+ | Melting Point (°C.) |
|---|---|---|---|---|---|---|---|
| 1 | 3-Cl—$C_6H_4$ | H | H | H | E | 7.59 | 82 |
| 2 | 3-Cl—$C_6H_4$ | H | H | H | Z | | |
| 3 | 3-Cl—$C_6H_4$ | H | $CH_3$ | H | E | 7.63 | Oil |
| 4 | 3-Cl—$C_6H_4$ | H | $CH_3$ | H | Z | | |
| 5 | 3-Cl—$C_6H_4$ | H | $CH_3$ | $CH_3$ | E | | |
| 6 | $C_6H_5$ | H | $C_2H_5$ | H | E | | |
| 7 | $C_6H_5$ | H | n-$C_3H_7$ | H | E | | |
| 8 | $C_6H_5$ | H | i-$C_3H_7$ | H | E | | |
| 9 | $C_6H_5$ | H | n-$C_4H_9$ | H | E | | |
| 10 | $C_6H_5$ | H | i-$C_4H_9$ | H | E | | |
| 11 | $C_6H_5$ | H | s-$C_4H_9$ | H | E | | |
| 12 | $C_6H_5$ | H | t-$C_4H_9$ | H | E | | |
| 13 | $C_6H_5$ | H | $CH_2$:CH | H | E | | |
| 14 | $C_6H_5$ | H | $CH_2$:$CHCH_2$ | ·H | E | | |
| 15 | $C_6H_5$ | H | E—$CH_3CH$:$CHCH_2$ | H | E | | |
| 16 | $C_6H_5$ | 3-$NO_2$ | H | H | E | | |
| 17 | $C_6H_5$ | 4-$CH_3$ | H | H | E | | |
| 18 | $C_6H_5$ | 5-F | H | H | E | | |
| 19 | $C_6H_5$ | 6-$CH_3O$ | H | H | E | | |
| 20 | $C_6H_5$ | 5-Cl | H | H | E | | |
| 21 | 2-F—$C_6H_4$ | 3-CN | H | H | E | | |
| 22 | 3-F—$C_6H_4$ | 4-$CH_2$:$CHCH_2$ | H | H | E | | |
| 23 | 4-Cl—$C_6H_4$ | H | H | H | E | 7.59 | 104 |
| 24 | 2-Br—$C_6H_4$ | H | H | H | E | 7.62 | 99-101 |
| 25 | 3-I—$C_6H_4$ | H | H | H | E | 7.59 | 116 |
| 26 | 4-$CH_3$—$C_6H_4$ | H | H | H | E | | |
| 27 | 2-$CH_3CH_2$—$C_6H_4$ | H | H | H | E | 7.61 | 49-50 |
| 28 | 3-($CH_3$)$_2$CH—$C_6H_4$ | H | H | H | E | | |
| 29 | 3-($CH_3$)$_3$C—$C_6H_4$ | H | H | H | E | 7.57 | Oil |
| 30 | 2-$CH_3O$—$C_6H_4$ | H | H | H | E | | |
| 31 | 3-$CF_3O$—$C_6H_4$ | H | H | H ' | E | | |
| 32 | 4-$C_6H_5O$—$C_6H_4$ | H | H | H | E | | |
| 33 | 2-$NO_2$—$C_6H_4$ | H | H | H | E | 7.62 | 90 |
| 34 | 3-$NH_2$—$C_6H_4$ | H | H | H | E | 7.59 | Gum |
| 35 | 4-$C_6H_5$—$C_6H_4$ | H | H | H | E | | |
| 36 | 2-$HO_2C$—$C_6H_4$ | H | H | H | E | | |
| 37 | 3-$CH_3O_2C$—$C_6H_4$ | H | H | H | E | 7.59 | Oil |
| 38 | 4-(CN)—$C_6H_4$ | H | H | H | E | 7.64 | 105 |
| 39 | 2-HO—$C_6H_4$ | H | H | H | E | | |
| 40 | 3-$CH_3C(O)NH$—$C_6H_4$ | H | H | H | E | | |
| 41 | 2,3-di-F—$C_6H_3$ | H | H | H | E | 7.60 | 60-62 |

TABLE I-continued

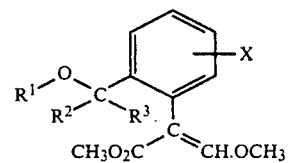

| COMPOUND No. | R¹ | X | R² | R³ | Isomer* | Olefinic+ | Melting Point (°C.) |
|---|---|---|---|---|---|---|---|
| 42 | 3,5-di-F—C₆H₃ | H | H | H | E | | |
| 43 | 2,4-di-Cl—C₆H₃ | H | H | H | E | 7.62 | 114 |
| 44 | 2,6-di-Cl—C₆H₃ | H | H | H | E | 7.62 | 103 |
| 45 | 3,4-di-Cl—C₆H₃ | H | H | H | E | 7.59 | 115 |
| 46 | 2,5-di-CH₃—C₆H₃ | H | H | H | E | | |
| 47 | 2,3-di-CH₃O—C₆H₃ | H | H | H | E | | |
| 48 | 2-F,4-Cl—C₆H₃ | H | H | H | E | | |
| 49 | 2-Cl,5-F—C₆H₃ | H | H | H | E | | |
| 50 | 2-F,6-CH₃—C₆H₄ | H | H | H | E | | |
| 51 | 3-CH₃,4-F—C₆H₃ | H | H | H | E | | |
| 52 | 3-F,5-CH₃O—C₆H₃ | H | H | H | E | | |
| 53 | 2-CH₃O,3-F—C₆H₃ | H | H | H | E | | |
| 54 | 2-Cl,4-CH₃—C₆H₃ | H | H | H | E | | |
| 55 | 2-CH₃,5-Cl—C₆H₃ | H | H | H | E | | |
| 56 | 2-Cl,6-CH₃O—C₆H₃ | H | H | H | E | | |
| 57 | 3-CH₃O,4-Cl—C₆H₃ | H | H | H | E | | |
| 58 | 3-CH₃,5-CH₃O—C₆H₃ | H | H | H | E | | |
| 59 | 2,4,6-tri-F—C₆H₂ | H | H | H | E | | |
| 60 | 2,4,6-tri-Cl—C₆H₂ | H | H | H | E | | |
| 61 | 2,4,6-tri-CH₃—C₆H₂ | H | H | H | E | | |
| 62 | 2,6-di-F,4-Cl—C₆H₂ | H | H | H | E | | |
| 63 | 2,6-di-Me,4-F—C₆H₂ | H | H | H | E | | |
| 64 | 2,3,5,6-tetra-Cl—C₆H | H | H | H | E | | |
| 65 | Pentafluorophenyl | H | H | H | E | | |
| 66 | Pentachlorophenyl | H | H | H | E | | |
| 67 | Pyridin-2-yl | H | H | H | E | 7.54 | 65–66 |
| 68 | Pyridin-3-yl | H | H | H | E | 7.60 | 77 |
| 69 | Pyridin-4-yl | H | H | H | E | | |
| 70 | 5-(trifluoromethyl)-pyridin-2-yl | H | H | H | E | | |
| 71 | Pyrimidin-2-yl | H | H | H | E | | |
| 72 | Pyrimidin-4-yl | H | H | H | E | | |
| 73 | Pyrimidin-5-yl | H | H | H | E | | |
| 74 | 3-Fluoropyridin-2-yl | H | H | H | E | | |
| 75 | 3-Chloropyridin-2-yl | H | H | H | E | | |
| 76 | 4-Bromopyridin-2-yl | H | H | H | E | | |
| 77 | 5-Methylpyridin-2-yl | H | H | H | E | | |
| 78 | 6-Methoxypyridin-2-yl | H | H | H | E | | |
| 79 | 2-Fluoropyridin-3-yl | H | H | H | E | | |
| 80 | 4-(Trifluoromethyl)pyridin-3-yl | H | H | H | E | | |
| 81 | 5-Methylpyridin-3-yl | H | H | H | E | | |
| 82 | 6-Methoxypyridin-3-yl | H | H | H | E | | |
| 83 | 2-Chloropyridin-4-yl | H | H | H | E | | |
| 84 | 3-(Trifluoromethyl)pyridin-4-yl | H | H | H | E | | |
| 85 | 4-Fluoropyrimidin-2-yl | H | H | H | E | | |
| 86 | 5-Methylpyridin-2-yl | H | H | H | E | | |
| 87 | 2-Chloropyrimidin-4-yl | H | H | H | E | | |
| 88 | 5-Methoxypyrimidin-4-yl | H | H | H | E | | |
| 89 | 6-(Trifluoromethyl)pyrimidin-4-yl | H | H | H | E | | |
| 90 | 2-Bromopyrimidin-5-yl | H | H | H | E | | |
| 91 | 4-Methylpyrimidin-5-yl | H | H | H | E | | |
| 92 | 3-Fluoro-5-(trifluoromethyl)-pyridin-2-yl | H | H | H | E | | |
| 93 | 3,6-Dichloro-5-(trifluoromethyl)-pyridin-2-yl | H | H | H | E | | |
| 94 | 6-Chloro-4-cyanopyridin-2-yl | H | H | H | E | | |
| 95 | 3-Cyano-5-nitropyridin-2-yl | H | H | H | E | | |
| 96 | 2-Chloro-6-fluoropyridin-4-yl | H | H | H | E | | |
| 97 | 4,6-Difluoropyridin-2-yl | H | H | H | E | | |
| 98 | 3,5-Dichloro-6-fluoropyridin-2-yl | H | H | H | E | | |
| 99 | 6-Methoxy-3-nitropyridin-2-yl | H | H | H | E | | |
| 100 | 4-Cyano-6-fluoropyridin-2-yl | H | H | H | E | | |
| 101 | 4-Cyano-3,5,6-trifluoropyridin-2-yl | H | H | H | E | | |
| 102 | 4-Cyano-2,5,6-trifluoropyridin-3-yl | H | H | H | E | | |
| 103 | 6-Chloro-5-nitropyridin-2-yl | H | H | H | E | | |
| 104 | 4,6-Dicyanopyridin-2-yl | H | H | H | E | | |
| 105 | 5-(Trichloromethyl)pyridin-2-yl | H | H | H | E | | |
| 106 | 5-Cyanopyridin-2-yl | H | H | H | E | | |
| 107 | 5-Bromo-4-(trifluoromethyl)pyridin-2-yl | H | H | H | E | | |
| | | H | H | H | E | | |
| 108 | 3-Nitro-5-(trifluoromethyl)pyridin-2-yl | H | H | H | E | | |
| 109 | 5-Formamidopyridin-2-yl | H | H | H | E | | |

TABLE I-continued

Structure: R¹−O−C(R²)(R³)−[phenyl with X]−C(CO₂CH₃)=CH.OCH₃

| COMPOUND No. | R¹ | X | R² | R³ | Isomer* | Olefinic+ | Melting Point (°C.) |
|---|---|---|---|---|---|---|---|
| 110 | 5-Aminopyridin-2-yl | H | H | H | E | | |
| 111 | 2,3,5,6-Tetrafluoropyridin-4-yl | H | H | H | E | | |
| 112 | 5-Nitropyridin-2-yl | H | H | H | E | | |
| 113 | 4-Methyl-5-nitropyridin-2-yl | H | H | H | E | | |
| 114 | 5-(Difluoromethyl)pyridin-2-yl | H | H | H | E | | |
| 115 | 5-(Fluoromethyl)pyridin-2-yl | H | H | H | E | | |
| 116 | 4,6-Difluoropyrimidin-2-yl | H | H | H | E | | |
| 117 | 2-Chloro-6-(trichloromethyl)pyrimidin-4-yl | H | H | H | E | | |
| 118 | 2,6-Dichloropyrimidin-4-yl | H | H | H | E | | |
| 119 | 5-(Methoxycarbonyl)pyridin-2-yl | H | H. | H | E | | |
| 120 | 5-Chloro-6-methoxypyridin-2-yl | H | H | H | E | | |
| 121 | 5,6-Dichloropyridin-2-yl | H | H | H | E | | |
| 122 | 6-Bromo-5-chloropyridin-2-yl | H | H | H | E | | |
| 123 | 5-Chloro-6-acetoxypyridin-2-yl | H | H | H | E | | |
| 124 | 5-Bromo-6-fluoropyridin-2-yl | H | H | H | E | | |
| 125 | 5-Bromo-6-cyanopyridin-2-yl | H | H | H | E | | |
| 126 | 5-Bromo-6-hydroxypyridin-2-yl | H | H | H | E | | |
| 127 | 5-Bromo-6-methoxypyridin-2-yl | H | H | H | E | | |
| 128 | 5,6-Dibromopyridin-2-yl | H | H | H | E | | |
| 129 | pyrazin-2-yl | H | H | H | E | | |
| 130 | 6-chloropyrazin-2-yl | H | H | H | E | | |
| 131 | 5-methylpyrazin-2-yl | H | H | H | E | | |
| 132 | pyridazin-3-yl | H | H | H | E | | |
| 133 | 6-chloropyridazin-3-yl | H | H | H | E | | |
| 134 | 1,2,3-triazin-4-yl | H | H | H | E | | |
| 135 | 1,2,4-triazin-5-yl | H | H | H | E | | |
| 136 | 1,2,4-triazin-6-yl | H | H | H | E | | |

TABLE I-continued

Structure: R¹O-C(R²)(R³)-[phenyl with X]-C(=CH.OCH₃)-CO₂CH₃

| COMPOUND No. | R¹ | X | R² | R³ | Isomer* | Olefinic+ | Melting Point (°C.) |
|---|---|---|---|---|---|---|---|
| 137 | 3-methyl-1,2,4-triazine (N=N, N) | H | H | H | E | | |
| 138 | 3-methyl-1,2,4-triazine isomer | H | H | H | E | | |
| 139 | thiophen-3-yl | H | H | H | E | | |
| 140 | thiophen-2-yl | H | H | H | E | | |
| 141 | 4-chlorothiophen-3-yl | H | H | H | E | | |
| 142 | 2-chlorothiophen-3-yl | H | H | H | E | | |
| 143 | 5-chlorothiophen-3-yl | H | H | H | E | | |
| 144 | 4-chlorothiophen-2-yl | H | H | H | E | | |
| 145 | 5-chlorothiophen-2-yl | H | H | H | E | | |
| 146 | Naphth-1-yl | H | H | H | E | | |
| 147 | Naphth-2-yl | H | H | H | E | | |
| 148 | quinolin-6-yl | H | H | H | E | | |
| 149 | quinolin-2-yl | H | H | H | E | 7.56 | 109–110 |

TABLE I-continued

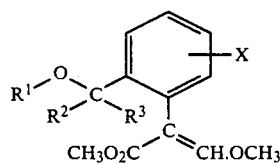

| COMPOUND No. | R¹ | X | R² | R³ | Isomer* | Olefinic+ | Melting Point (°C.) |
|---|---|---|---|---|---|---|---|
| 150 | isoquinolin-6-yl | H | H | H | E | | |
| 151 | quinoxalin-6-yl | H | H | H | E | | |
| 152 | quinoxalin-2-yl | H | H | H | E | | |
| 153 | benzothiophen-3-yl | H | H | H | E | | |
| 154 | benzothiophen-5-yl | H | H | H | E | | |
| 155 | 3-F—C₆H₄ | H | H | H | E | 7.59 | 102 |
| 156 | 4-F—C₆H₄ | H | H | H | E | 7.61 | 102 |
| 157 | 2-Cl—C₆H₄ | H | H | H | E | 7.61 | 88 |
| 158 | 2,5-di-Cl—C₆H₃ | H | H | H | E | 7.63 | 118 |
| 159 | 4-Br—C₆H₄ | H | H | H | E | 7.58 | 118 |
| 160 | 3-CH₃O—C₆H₄ | H | H | H | E | 7.58 | Oil |
| 161 | 3-NO₂—C₆H₄ | H | H | H | E | 7.63 | 116 |
| 162 | 3,5-di-Cl—C₆H₃ | H | H | H | E | 7.64 | 113 |
| 163 | 2,3-di-Cl—C₆H₃ | H | H | H | E | 7.62 | 92 |
| 164 | 3-CH₃—C₆H₄ | H | H | H | E | 7.6 | 62 |
| 165 | 3-C₆H₅O—C₆H₄ | H | H | H | E | 7.56 | Oil |
| 166 | 3-Br—C₆H₄ | H | H | H | E | 7.60 | 105 |
| 167 | 3-Cl—5-CH₃O—C₆H₃ | H | H | H | E | 7.60 | 71 |
| 168 | 3-CF₃—C₆H₄ | H | H | H | E | 7.60 | 40 |
| 169 | 3-(C₂H₅)₂N—C₆H₄ | H | H | H | E | 7.58 | Oil |
| 170 | 3-C₂H₅O, 4-CH₃O—C₆H₃ | H | H | H | E | 7.57 | 98 |
| 171 | 3-HO—C₆H₄ | H | H | H | E | 7.60 | Oil |
| 172 | 3-(3-CH₃O—C₆H₄)—C₆H₄ | H | H | H | E | 7.57 | Oil |
| 173 | 3-(2-CH₃O—C₆H₄O)—C₆H₄ | H | H | H | E | 7.57 | Oil |
| 174 | 4-(Trifluoromethyl)pyridin-2-yl | H | H | H | E | 7.57 | Gum |
| 175 | 3-Formyl-C₆H₄ | H | H | H | E | 7.61 | Oil |
| 176 | 6-Bromopyridin-2-yl | H | H | H | E | 7.57 | 62–64 |
| 177 | 6-(Trifluoromethyl)pyridin-2-yl | H | H | H | E | 7.56 | 68–69 |
| 178 | 3-HOCH₂—C₆H₄ | H | H | H | E | 7.60 | Gum |
| 179 | 3-((E)—C₆H₅H═CH)—C₆H₄ | H | H | H | E | 7.60 | Gum |
| 180 | 3-((E)—C₆H₅CH═N)—C₆H₄ | H | H | H | E | 7.59 | Gum |
| 181 | 3-(3-CH₃)—C₆H₄O)—C₆H₄ | H | H | H | E | 7.57 | Oil |
| 182 | 3-(2-Cl—C₆H₄O)—C₆H₄ | H | H | H | E | 7.57 | Oil |
| 183 | 3-(3-Br—C₆H₄O)—C₆H₄ | H | H | H | E | 7.58 | Oil |
| 184 | 3-C₆H₅CH₂O—C₆H₄ | H | H | H | E | 7.57 | Oil |
| 185 | 6-Phenoxypyridin-2-yl | H | H | H | E | 7.50 | 58–59 |
| 186 | 3-C₆H₅OCH₂—C₆H₄ | H | H | H | E | 7.59 | Oil |
| 187 | 3-NO₂, 5-C₆H₅O—C₆H₃ | H | H | H | E | 7.63 | Gum |
| 188 | 3-Cl, 5-C₆H₅O—C₆H₃ | H | H | H | E | 7.59 | Gum |

TABLE I-continued

Structure:
R¹O—C(R²)(R³)—[phenyl with X substituent]—C(CO₂CH₃)=CH.OCH₃

| COMPOUND No. | R¹ | X | R² | R³ | Isomer* | Olefinic+ | Melting Point (°C.) |
|---|---|---|---|---|---|---|---|
| 189 | dibenzofuran-2-yl (attached via methylene) | H | H | H | E | 7.62 | 127–128 |
| 190 | dibenzofuran-3-yl | H | H | H | E | | |
| 191 | dibenzo[1,4]dioxin-yl | H | H | H | E | | |
| 192 | 3-Br, 4-F—$C_6H_3$ | H | H | H | E | | |
| 193 | 3-$CF_3$, 4-Cl—$C_6H_3$ | H | H | H | E | | |
| 194 | 3-$C_6H_5O$, 4-Cl—$C_6H_3$ | H | H | H | E | | |
| 195 | 3-$(CH_3)_3C$, 4-$CH_3O$—$C_6H_3$ | H | H | H | E | | |
| 196 | 3-$CH_3CH_2O$—$C_6H_4$ | H | H | H | E | | |
| 197 | 3,5-di-$CH_3O$—$C_6H_3$ | H | H | H | E | | |
| 198 | 3-$CH_3O$, 5-$CH_3CH_2O$—$C_6H_3$ | H | H | H | E | | |
| 199 | 3-$(CH_3)_3CO$—$C_6H_4$ | H | H | H | E | | |
| 200 | 3-$(CH_3)_3CO$, 4-$CH_3O$—$C_6H_3$ | H | H | H | E | | |
| 201 | 2,4-di-F—$C_6H_3$ | H | H | H | E | | |
| 202 | 2,5-di-F—$C_6H_3$ | H | H | H | E | | |
| 203 | 2-Cl, 4-F—$C_6H_3$ | H | H | H | E | | |
| 204 | 2-F, 5-Cl—$C_6H_3$ | H | H | H | E | | |
| 205 | 2-Cl, 4-$CH_3O$—$C_6H_3$ | H | H | H | E | | |
| 206 | 2-$CH_3O$, 4-Cl—$C_6H_3$ | H | H | H | E | | |
| 207 | 2-Cl, 5-$CH_3O$—$C_6H_3$ | H | H | H | E | | |
| 208 | 2-$CH_3O$, 5-Cl—$C_6H_3$ | H | H | H | E | | |
| 209 | 2-Br, 4-F—$C_6H_3$ | H | H | H | E | | |
| 210 | 2-F, 4-Br—$C_6H_3$ | H | H | H | E | | |
| 211 | 2-Br, 5-F—$C_6H_3$ | H | H | H | E | | |
| 212 | 2-F, 5-Br—$C_6H_3$ | H | H | H | E | | |
| 213 | 3-$HO_2C$—$C_6H_4$ | H | H | H | E | 7.61 | 117–123 |
| 214 | 3-(pyrimidin-2-yloxy)phenyl | H | H | H | E | 7.58 | 157–165 |
| 215 | 3-(5-chloropyrimidin-2-yloxy)phenyl | H | H | H | E | 7.58 | 126–127 |
| 216 | 3-(pyridin-2-yloxy)phenyl | H | H | H | E | | |
| 217 | 3-(5-trifluoromethylpyridin-2-yloxy)phenyl | H | H | H | E | | |

TABLE I-continued $$\underset{CH_3O_2C}{\overset{R^1-O}{\underset{R^2}{\bigg|}}\underset{R^3}{C}}\overset{\displaystyle\bigcirc-X}{\underset{CH.OCH_3}{C}}$$

| COMPOUND No. | R¹ | X | R² | R³ | Isomer* | Olefinic⁺ | Melting Point (°C.) |
|---|---|---|---|---|---|---|---|
| 218 | (5-CF₃-pyridin-2-yl)oxy-(4-methylphenyl) | H | H | H | E | 7.60 | 75–76 |
| 219 | 3-Allyloxy-C₆H₄ | H | H | H | E | | |
| 220 | 3-Propargyloxy-C₆H₄ | H | H | H | E | | |
| 221 | 3-C₆H₅.CO₂—C₆H₄ | H | H | H | E | | |
| 222 | 3-C₆H₅.SO₂O—C₆H₄ | H | H | H | E | | |
| 223 | 3-ClCH₂C₆H₄ | H | H | H | E | | |
| 224 | 3-BrCH₂C₆H₄ | H | H | H | E | | |
| 225 | 3-C₆H₅CH₂CH₂C₆H₄ | H | H | H | E | | |
| 226 | 3-(E)—C₆H₅CH:CH.C₆H₄ | H | H | H | E | 7.59 | Oil |
| 227 | 3-C₆H₅CO.C₆H₄ | H | H | H | E | | |
| 228 | 3-C₆H₅.CH(OH).C₆H₄ | H | H | H | E | | |
| 229 | 3-C₆H₅.CH₂.C₆H₄ | H | H | H | E | | |
| 230 | 3-C₆H₅O₂C.C₆H₄ | H | H | H | E | | |
| 231 | 3-C₆H₅N(CH₃)CO.C₆H₄ | H | H | H | E | | |
| 232 | 3-(4-Cl—C₆H₄)CH₂C₆H₄ | H | H | H | E | 7.57 | Oil |
| 233 | benzo[1,3]dioxol-4-yl | H | H | H | E | | |
| 234 | benzo[1,3]dioxol-5-yl | H | H | H | E | | |
| 235 | 3-(3,5-di-Cl—C₆H₃O)—C₆H₄ | H | H | H | E | | |
| 236 | 3-(2,4-di-Cl—C₆H₃O)—C₆H₄ | H | H | H | E | | |
| 237 | 4-Phenylpyridin-2-yl | H | H | H | E | | |
| 238 | 6-Phenylpyridin-2-yl | H | H | H | E | | |
| 239 | 4-Phenoxypyridin-2-yl | H | H | H · | E | | |
| 240 | 3-Chloro-5-(trifluoromethyl)pyridin-2-yl | H | H | H | E | | |
| 241 | 6-Hydroxypyridin-2-yl | H | H | H | E | | |
| 242 | 6-Ethoxypyridin-2-yl | H | H | H | E | | |
| 243 | 6-Benzyloxypyridin-2-yl | H | H | H | E | | |
| 244 | 6-Chloropyridin-2-yl | H | H | H | E | | |
| 245 | 6-Methylpyridin-2-yl | H | H | H | E | | |
| 246 | 4-Benzyloxypyridin-2-yl | H | H | H | E | | |
| 247 | 4,6-Di(trifluoromethyl)pyridin-2-yl | H | H | H | E | | |
| 248 | 2-(Carboxymethyl)phenyl | H | H | H | E | | |
| 249 | 2-(Methoxycarbonylmethyl)phenyl | H | H | H | E | | |
| 250 | 2-[C(CO₂CH₃)=CHOCH₃]phenyl | H | H | H | E | | |
| 251 | 6-Formylpyridin-2-yl | H | H | H | E | | |
| 252 | 6-Aminopyridin-2-yl | H | H | H | E | | |
| 253 | 4-Aminopyridin-2-yl | H | H | H | E | | |
| 254 | 4-Carboxypyridin-2-yl | H | H | H | E | | |

⁺Chemical shift of singlet from olefinic proton on beta-methoxypropenoate group (ppm from tetramethylsilane.)
Solvent CDCl₃ unless otherwise stated.
*Geometry of beta-methoxypropenoate group.

The invention is also illustrated by the compounds of the formula:

compounds in Table I (i.e. where Y of Compound (I) is oxygen) and $R^4$ is (a) hydrogen and (b) methyl.

In addition, $R^1$, $R^2$, $R^3$, $R^4$ and X may have the meanings given in Table III below.

TABLE III

| COMPOUND NO. | $R^1$ | X | $R^2$ | $R^3$ | $R^4$ | Isomer* | Olefinic+ | Melting Point (°C.) |
|---|---|---|---|---|---|---|---|---|
| 1 | $C_6H_5$ | H | H | H | H | E | | |
| 2 | $C_6H_5$ | H | H | H | $CH_3$ | E | 7.54 | 115–121 |
| 3 | $C_6H_5$ | H | H | H | $C_2H_5$ | E | | |
| 4 | $C_6H_5$ | H | H | H | n-$C_3H_7$ | E | | |
| 5 | $C_6H_5$ | H | H | H | i-$C_3H_7$ | E | | |
| 6 | $C_6H_5$ | H | H | H | n-$C_4H_9$ | E | | |
| 7 | $C_6H_5$ | H | H | H | i-$C_4H_9$ | E | | |
| 8 | $C_6H_5$ | H | H | H | s-$C_4H_9$ | E | | |
| 9 | $C_6H_5$ | H | H | H | t-$C_4H_9$ | E | | |
| 10 | $C_6H_5$ | H | H | H | $CH_2$:CH | E | | |
| 11 | $C_6H_5$ | H | H | H | $CH_2$:$CHCH_2$ | E | | |
| 12 | $C_6H_5$ | H | H | H | H | Z | | |
| 13 | $C_6H_5$ | H | H | H | $CH_3$ | Z | | |
| 14 | $C_6H_5$ | H | H | H | $C_2H_5$ | Z | | |
| 15 | $C_6H_5$ | H | $CH_3$ | H | H | E | | |
| 16 | $C_6H_5$ | H | $CH_3$ | H | $CH_3$ | E | | |
| 17 | $C_6H_5$ | H | $CH_3$ | $CH_3$ | H | E | | |
| 18 | $C_6H_5$ | H | $CH_3$ | $CH_3$ | $CH_3$ | E | | |

+Chemical shift or singlet from olefinic on beta-methoxypropenoate group (ppm from tetramethylsilane); Solvent $CDCl_3$ unless otherwise stated.
*Geometry of beta-methoxypropenoate group.

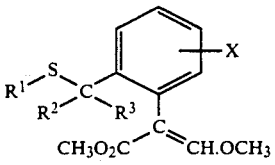

in which $R^1$, $R^2$, $R^3$ and X have the same combinations of meanings as each of the corresponding oxygen-linked compounds in Table I (i.e. when Y of Compound (I) is oxygen) and the meanings given to Compounds Nos. 1 to 3 in Table II below.

Compound No. 4 of Table II corresponds to Compound No. 1 of Table I and Compound No. 5 corresponds to Compound No. 67 of Table I with respect to their meanings of $R^1$, $R^2$, $R^3$ and X.

TABLE II

| COMPOUND NO. | $R^1$ | X | $R^2$ | $R^3$ | Isomer* | Olefinic+ | Melting Point (°C.) |
|---|---|---|---|---|---|---|---|
| 1 | $C_6H_5$ | H | H | H | E | 7.60 | 69 |
| 2 | $C_6H_5$ | H | $CH_3$ | H | E | | |
| 3 | $C_6H_5$ | H | $CH_3$ | $CH_3$ | E | | |
| 4 | 3-Cl—$C_6H_4$ | H | H | H | E | 7.60 | 85 |
| 5 | Pyridin-2-yl | H | H | H | E | 7.57 | Oil |

+Chemical shift of singlet from olefinic proton on beta-methoxypropenoate group (ppm from tetramethylsilane).
Solvent $CDCl_3$ unless otherwise stated.
*Geometry of beta-methoxypropenoate group.

The invention is further illustrated by the compounds of the formula:

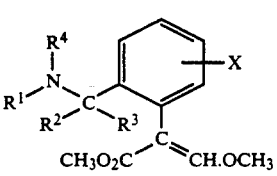

in which $R^1$, $R^2$, $R^3$ and X have the same combinations of meanings as each of the corresponding oxygen-linked

TABLE IV

TABLE IV: SELECTED PROTON NMR DATA

Table IV shows selected proton NMR data for certain compounds described in Tables I and II. Unless otherwise indicated, compounds are from Table I. Chemical shifts are measured in ppm from tetramethylsilane, and deuterochloroform was used as solvent throughout. The following abbreviations are used:

| br = broad | t = triplet | ppm = parts per million |
|---|---|---|
| s = singlet | q = quartet | |
| d = doublet | m = multiplet | |

| COMPOUND NO. | |
|---|---|
| 29 | 1.28 (9H, s), 3.69 (3H, s), 3.81 (3H, s), 4.94 (2H, s), 6.7 (1H, m), 6.95 (2H, m), 7.15–7.4 (4H, m), 7.55 (1H, m), 7.57 (1H, s) ppm. |
| 37 | 3.70 (3H, s), 3.82 (3H, s), 3.90 (3H, s), 5.00 (2H, s), 7.04–7.36 (5H, m), 7.55–7.62 (3H, m), 7.59 (1H, s) ppm. |
| 160 | 3.70 (3H, s), 3.76 (3H, s), 3.82 (3H, s), 4.94 (2H, s), 6.5 (3H, m), 7.16 (2H, m), 7.35 (2H, m), 7.55 (1H, m), 7.58 (1H, s) ppm. |
| 169 | 1.13 (6H, t), 3.31 (4H, q), 3.70 (1H, s), 3.82 (3H, s), 4.94 (2H, s), 6.2–6.35 (3H, m), 7.05–7.4 (4H, m), 7.56 (1H, m), 7.58 (1H, s) ppm. |
| 170 | 1.42 (3H, t), 3.69 (3H, s), 3.82 (6H, s), 4.05 (2H, q), 4.90 (2H, s), 6.36 (1H, m), 6.54 (1H, m), 6.74 (1H, m), 7.17 (1H, m), 7.32 (2H, m), 7.54 (1H, m), 7.57 (1H, s) ppm. |
| 172 | 3.70 (3H, s), 3.79 (3H, s), 3.82 (3H, s), 4.93 (2H, s), 6.5–6.7 (6H, m), 7.1–7.4 (5H, m), 7.52 (1H, m), 7.57 (1H, s) ppm. |
| 173 | 3.67 (3H, s), 3.79 (3H, s), 3.83 (3H, s), 4.91 (2H, s), 6.45–6.64 (3H, m), 6.88–7.38 (8H, m), 7.52 (1H, m), 7.57 (1H, s) ppm. |
| 174 | 3.68 (3H, s), 3.81 (3H, s), 5.31 (2H, s), 6.96 (1H, s), 7.07 (1H, d), 7.19 (1H, m), 7.30–7.40 (2H, m), 7.51–7.61 (1H, m), 7.57 (1H, s), 8.29 (1H, d) ppm. |
| 179 | 3.71 (3H, s), 3.83 (3H, s), 5.04 (2H, s), 7.01–7.05 (1H, m), 7.17–7.62 (12H, |

TABLE IV: SELECTED PROTON NMR DATA (continued)

| | |
|---|---|
| | m), 7.60 (1H, s), 8.41 (1H, s) ppm. |
| 181 | 2.32 (3H, s), 3.67 (3H, s), 3.79 (3H, s), 4.93 (2H, s), 7.57 (1H, s) ppm. |
| 182 | 3.67 (3H, s), 3.78 (3H, s), 4.93 (2H, s), 6.5 (2H, m), 6.65 (1H, m), 6.9–7.55 (9H, m), 7.57 (1H, s) ppm. |
| 183 | 3.67 (3H, s), 3.78 (3H, s), 4.94 (2H, s), 6.55 (2H, m), 6.68 (1H, m), 6.90 (1H, m), 7.10–7.38 (7H, m), 7.5 (1H, m), 7.58 (1H, s) ppm. |
| 184 | 3.68 (3H, s), 3.78 (3H, s), 4.94 (2H, s), 5.02 (2H, s), 6.55 (3H, m), 7.1–7.45 (9H, m), 7.55 (1H, m), 7.57 (1H, s) ppm. |
| 187 | 3.70 (3H, s), 3.83 (3H, s), 5.02 (2H, s), 6.84 (1H, m), 7.04 (2H, m), 7.20 (2H, m), 7.33–7.49 (7H, m), 7.63 (1H, s) ppm. |
| 188 | 3.68 (3H, s), 3.82 (3H, s), 4.92 (2H, s), 6.45 (1H, m), 6.52 (1H, m), 6.61 (1H, m), 7.00–7.50 (9H, m), 7.59 (1H, s) ppm. |
| 226 | 3.72 (3H, s), 3.83 (3H, s), 5.01 (2H, s), 6.81 (1H, d), 7.04–7.39 (11H, m), 7.48–7.58 (3H, m), 7.59 (1H, s) ppm. |
| 232 | 3.68 (3H, s), 3.78 (3H, s), 3.88 (2H, s), 4.92 (2H, s), 6.68–6.77 (3H, m), 7.04–7.38 (8H, m), 7.48–7.55 (1H. m), 7.57 (1H, s) ppm. |
| 5 (of Table II) | 3.70 (3H, s), 3.83 (3H, s), 4.36 (2H, s), 6.94–7.00 (1H, m), 7.08–7.16 (2H, m), 7.22–7.30 (2H, m), 7.40–7.56 (2H, m), 7.57 (1H, s), 8.43 (1H, ddd) ppm. |

The compounds of the invention of formula (I) may be prepared by the steps shown in Schemes I to V. Throughout these Schemes the terms $R^1$, $R^2$, $R^3$, $R^4$, X and Y are as defined above, $R^5$ is hydrogen or a metal (such as sodium or potassium), R is an alkyl group, L is a leaving group such as halide (chloride, bromide or iodide), a $CH_3SO_4$-anion, or a sulphonyloxy-anion, and Z is a halogen (iodine, bromine or chlorine). Each of the transformations described in Schemes I to IV is performed at a suitable temperature and usually, though not always, in a suitable solvent.

The compounds of the invention of formula (I) can be prepared from the phenylacetates of formula (III) or the ketoesters of formula (VI) by the steps shown in Scheme I.

Thus compounds of formula (I) can be prepared by treatment of phenylacetates of formula (III) with a base (such as sodium hydride or sodium methoxide) and methyl formate. If a species of formula $CH_3L$, wherein L is as defined above, is then added to the reaction mixture, compounds of formula (I) may be obtained. If a protic acid is added to the reaction mixture, compounds of formula (II) wherein $R^5$ is hydrogen are obtained. Alternatively, the species of formula (II) wherein $R^5$ is a metal (such as sodium) may themselves be isolated from the reaction mixture.

Compounds of formula (II) wherein $R^5$ is a metal can be converted into compounds of formula (I) by treatment with a species of formula $CH_3L$, wherein L is as defined above. Compounds of formula (II) wherein $R^5$ is hydrogen can be converted into compounds of formula (I) by successive treatments with a base (such as potassium carbonate) and a species of general formula $CH_3L$.

Alternatively, compounds of formula (I) can be prepared from acetals of formula (IV) by elimination of methanol under either acidic or basic conditions. Examples of reagents or reagent mixtures which can be used for this transformation are lithium di-isopropylamide; potassium hydrogen sulphate (see, for example, T Yamada, H Hagiwara and H Uda, *J.Chem.Soc., Chemical Communications*, 1980, 838, and references therein); and triethylamine, often in the presence of a Lewis acid such as titanium tetrachloride (see, for example, K Nsunda and L Heresi, *J.Chem.Soc., Chemical Communications*, 1985, 1000).

Acetals of formula (IV) can be prepared by treatment of methyl silyl ketene acetals of formula (V) wherein R is an alkyl group, with trimethyl orthoformate in the presence of a Lewis acid such as titanium tetrachloride (see, for example, K Saigo, M Osaki and T Mukaiyama, *Chemistry Letters*, 1976, 769).

Methyl silyl ketene acetals of formula (V) can be prepared from phenylacetates of formula (III) by treatment with a base and a trialkylsilyl halide of formula $R_3SiCl$ or $R_3SiBr$, such as trimethylsilyl chloride, or a base (such as triethylamine) and a trialkylsilyl triflate of formula $R_3Si-OSO_2CF_3$ (see, for example, C Ainsworth, F Chen and Y Kuo, *J.Organometallic Chemistry*, 1972, 46, 59).

It is not always necessary to isolate the intermediates (IV) and (V); under appropriate conditions, compounds of formula (I) may be prepared from phenylacetates of formula (III) in "one pot" by the successive addition of suitable reagents listed above.

Alternatively, compounds of formula (I) can be prepared by treatment of ketoesters of formula (VI) with methoxymethylenation reagents such as methoxymethylenetriphenylphosphorane (see, for example, W Steglich, G Schramm, T Anke and F Oberwinkler, EP 0044448, 4.7.1980).

Ketoesters of formula (VI) may be prepared by methods described in the literature. Particularly useful methods include (i) the reaction of appropriate phenylmagnesium halides or phenyl-lithium species with dimethyl oxalate using the method described by L M Weinstock, R B Currie and A V Lovell, *Synth.Commun.*, 1981, 11, 943 and references therein; (ii) oxidation of phenylacetates of formula (III) using selenium dioxide, generally in the absence of a solvent, and generally at a temperature above 100° C.; and (iii) oxidation of mandelic acid esters using, for example, manganese oxide in a suitable solvent.

Scheme I

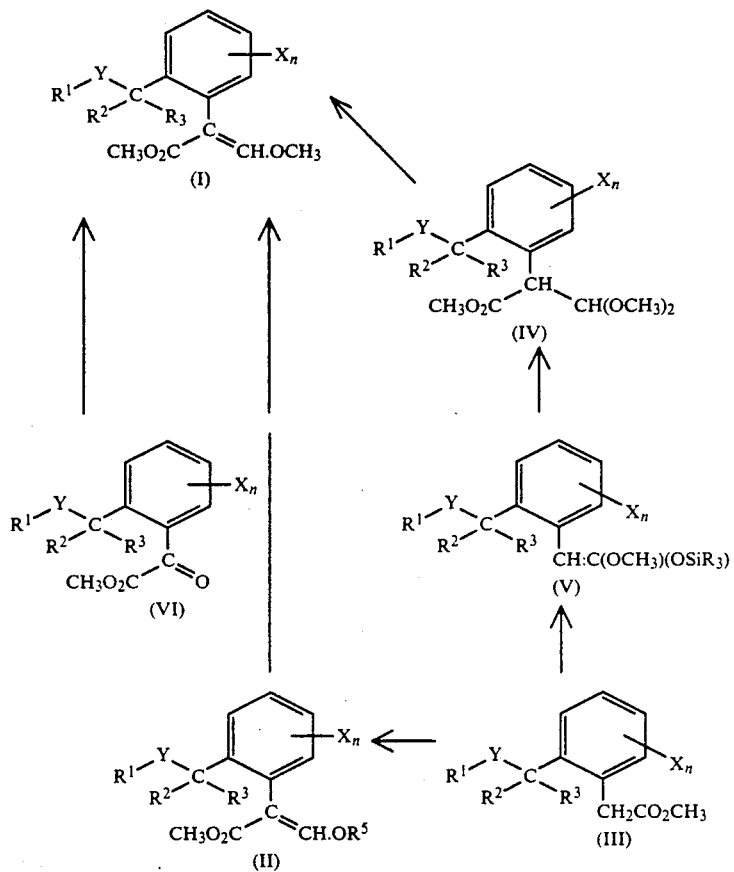

Scheme II shows approaches by which phenylacetates of formula (III) may be prepared from 3-isochromanones of formula (IX).

Thus treatment of isochromanones of formula (IX) with species of formula R¹YM, wherein R¹ and Y are as defined above and M is a metal (such as sodium or potassium), gives phenylacetic acids of formula (VIII). The phenylacetic acids (VIII) may be converted into phenylacetates (III) by standard methods described in the literature.

Alternatively, isochromanones of formula (IX) may be converted into phenylacetates of formula (VII) wherein Z is a halogen atom (such as bromine) using HZ in methanol. This transformation may also be accomplished in 2 steps if the isochromanone (IX) is treated with HZ in a nonalcoholic solvent, and the resulting phenylacetic acid is then esterified using standard procedures (see, for example, I Matsumoto and J Yoshizawa, Jpn. Kokai (Tokkyo Koho) 79 138 536, 27.10.1979, Chem.Abs., 1980, 92, 180829h; and G M F Lim, Y G Perron and R D Droghini, Res.Discl., 1979, 188, 672, Chem.Abs., 1980, 92, 128526t). Phenylacetates of formula (VII) may be converted into phenylacetates of formula (III) by treatment with species R¹YM, wherein R¹, Y and M are as defined above.

Phenylacetates of formula (III) and the corresponding phenylacetic acids of formula (VIII) may also be prepared by numerous other methods described in the chemical literature. For example, several useful methods are described by D C Atkinson, K E Godfrey, B Meek, J F Saville and M R Stillings, J.Med.Chem., 1983, 26, 1353 and D C Atkinson, K E Godfrey, P L Meyers, N C Phillips, M R Stillings and A P Welbourn, J.Med.- Chem., 1983, 26, 1361. Furthermore, many of the methods described for the preparation of 2-arylpropionic esters and acids by J-P Rieu, A Boucherie, H Cousse and G Mouzin, Tetrahedron, 1986, 42, 4095, are also applicable to the preparation of phenylacetates of formula (III) and phenylacetic acids of formula (VIII) using appropriate precursors wherein the substituents (R¹Y)R²R³C- and X are already present.

Scheme II

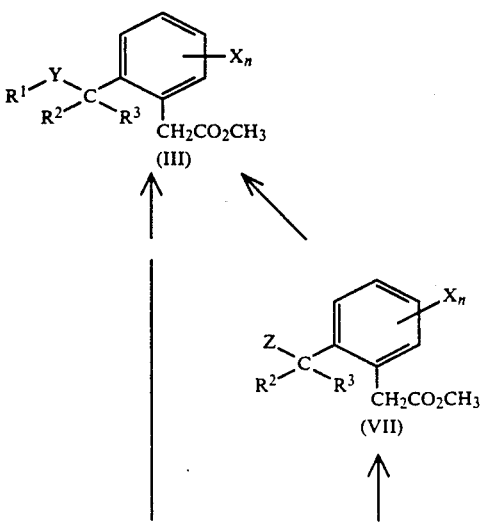

-continued
Scheme II

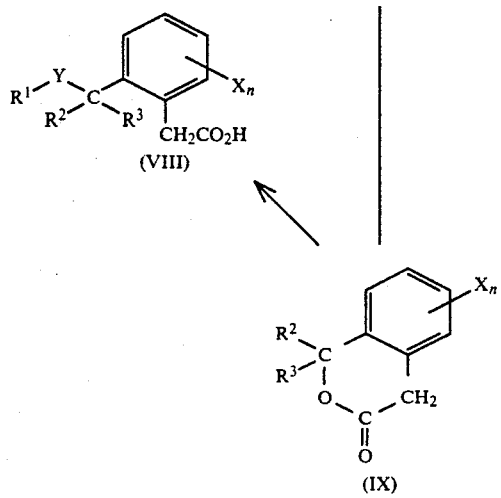

Isochromanones of formula (IX) may be prepared by methods described in the literature (see, for example, V B Milevskaya, R V Belinskaya, and L M Yagupol'skii, Zh.Org.Khim., 1973, 9, 2145; Chem.Abs., 80, 36954e).

Scheme III illustrates approaches to compounds of formula (I) from precursors containing a methyl beta-methoxypropenoate group. Thus propenoates of formula (X) are converted into compounds of formula (I) on treatment with species of formula $R^1YM$, wherein $R^1$, Y and M are as defined above. When $R^1$ is an optionally substituted heteroaryl group containing at least one nitrogen atom (such as an optionally substituted pyridinyl group), species of formula $R^1YM$ may be ambident nucleophiles and as such may in principle react at either nitrogen or Y. For example, metal salts of 2-hydroxypyridine can react with alkylating agents at either nitrogen or oxygen to give the corresponding N-alkylpyridone or the 2-alkoxypyridine products, respectively. In this case, selective substitution on Y may be achieved using methods outlined in the literature (see, for example, G C Hopkins, J P Jonak, H J Minnemeyer and H Tieckelmann, J.Org.Chem., 1967, 32 4040). Compounds of formula (X) wherein L is a halogen such as bromine or chlorine may be prepared by halogenation of alkylbenzenes of formula (XII) using, for example, N-bromosuccinimide or sulphuryl chloride and methods described in the literature (see, for example, Modern Synthetic Reactions, Herbert House, 2nd Edition, Benjamin/Cummings, p.478 and references therein, and H.Matsumoto et al., Chemistry Letters, 1978, pp. 223-226). Compounds of formula (X) wherein L is a sulphonyloxy-group may be prepared from benzyl alcohols of formula (XI) using a sulphonyl halide and methods described in the literature. Treatment of benzyl alcohols with sulphonyl halides in the presence of a base sometimes leads, via a sulphonyloxy-derivative, to a benzyl halide, and this constitutes an alternative approach to compounds of formula (X) wherein L is a halogen.

Alternatively, when $R^1$ is a sufficiently activated aryl or heteroaryl group, compounds of formula (I) may be prepared from compounds of formula (XIII) and species of formula $R^1L$, wherein $R^1$ and L are as defined above, often in the presence of a base such as sodium hydride, potassium tert-butoxide, or potassium carbonate.

The intermediates of formulae (XI), (XII) and (XIII) may be prepared from suitable phenylacetate or benzoylformate precursors using the transformations shown in Scheme I and described in the paragraphs above which refer to Scheme I.

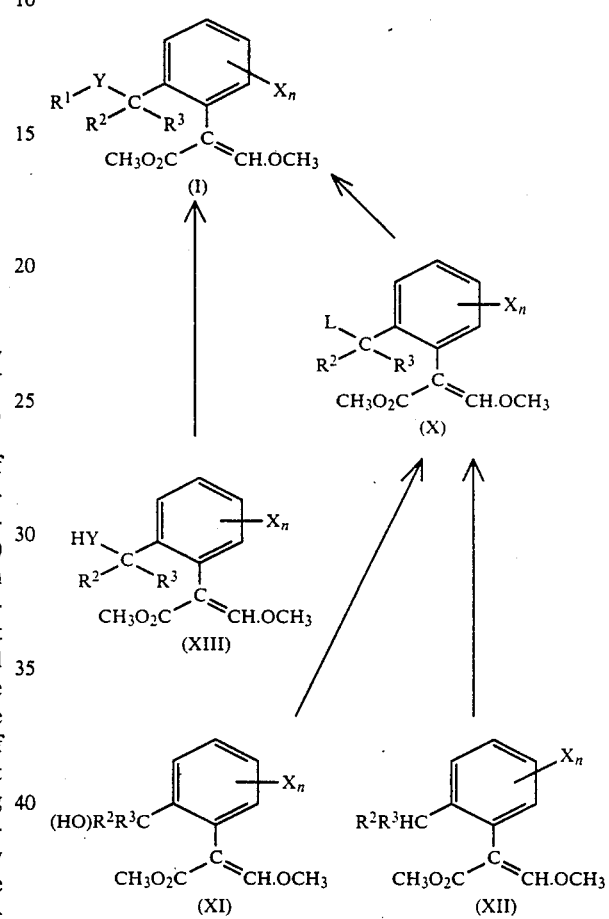

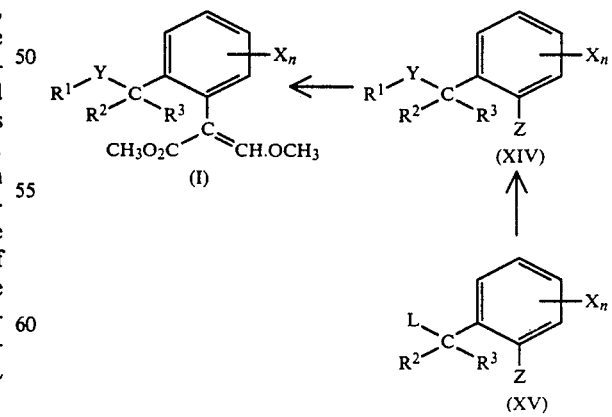

Some of the transformations shown in Scheme III can also be performed on intermediates containing, instead of the methyl beta-methoxypropenoate group, a group which can subsequently be converted into the methyl beta-methoxypropenoate group. For example, Scheme IV shows how the method used to transform (X) into (I) (Scheme III) can also be used to transform the halobenzene (XV) into the halobenzene (XIV) which can subsequently be converted into the compounds (I) using steps described in the paragraphs above or in the literature.

Scheme V

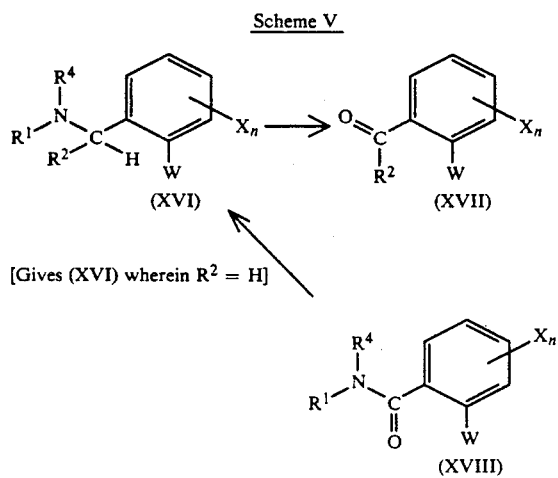

When the term Y has the value NR⁴, additional approaches for the preparation of compounds of formula (I) are available, and these are shown in Scheme V. In Scheme V the term W is either the alpha-linked methyl beta-methoxypropenoate group $CH_3O.CH{:}C(CO_2CH_3)$—, or it is a group or atom which may be converted into this group by the steps described in the paragraphs above, which is compatible with the conditions of the transformations of Scheme V.

Thus amides of formula (XVIII) may be reduced to amines of formula (XVI wherein $R^2=H$) using reducing agents such as lithium aluminum hydride; and carbonyl compounds of formula (XVII) may be converted into amines of formula (XVI) by treatment with a primary or secondary amine of formula $R^1R^4NH$, wherein $R^1$ and $R^4$ are defined as above, in the presence of hydrogen and a hydrogenation catalyst or another reducing agent (see J March, 'Advanced Organic Chemistry: Reactions, Mechanisms and Structure', 1968, McGraw-Hill Kogakusha Ltd, pages 668–670).

In further aspects the invention provides processes as hereindescribed for preparing the compounds of formula (I) and the intermediate chemicals of formulae (II) to (VI) and (VIII) used therein.

It also provides as intermediate chemicals the compounds of the formula (Ig):

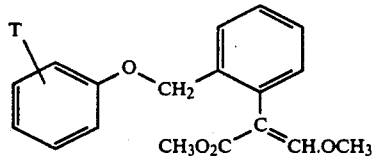 (Ig)

in which T is hydroxy, mercapto, formyl, hydroxymethyl, chloromethyl, bromomethyl, amino, carboxy or —CH₂NHR in which R is alkyl or aryl (especially $C_{1-4}$ alkyl or phenyl). These compounds include, in particular, the (E)-isomers.

It further provides as intermediate chemicals the compounds of the formula (Ih):

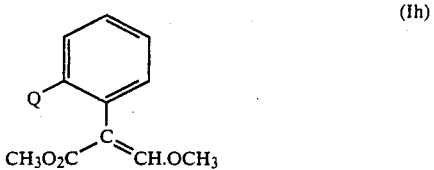 (Ih)

in which Q is chloromethyl or formyl. These compounds include, in particular, the (E)-isomers.

The compounds of the invention are active fungicides and may be used to control one or more of the following pathogens:

*Pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines.

*Helminthosporium* spp., *Rhynchosporium* spp., *Septoria* spp., *Pseudocercosporella herpotrichoides* and *Gaeumannomyces graminis* on cereals.

*Cercospora arachidicola* and *Cercosporidium personata* on peanuts and other *Cercospora* species on other hosts for example sugar beet, bananas, soya beans and rice.

*Botrytis cinerea* (grey mould) on tomatoes, strawberries, vegetables, vines and other hosts.

Alternaria species on vegetables (e.g. cucumber), oil-seed rape, apples, tomatoes and other hosts.

*Venturia inaequalis* (scab) on apples.

*Plasmopara viticola* on vines.

Other downy mildews such as *Bremia lactucae* on lettuce, Peronospora spp. on soybeans, tobacco, onions and other hosts and *Pseudoperonospora humuli* on hops and *Pseudoperonospora cubensis* on cucurbits.

*Phytophthora infestans* on potatoes and tomatoes and other Phytophthora spp. on vegetables, strawberries, avocado, pepper, ornamentals, tobacco, cocoa and other hosts. *Thanatephorus cucumeris* on rice and other Rhizoctonia species on various host such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further some of the compounds may be active as seed dressings against Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

Some of the compounds can move acropetally and locally in the plant tissue. Moreover, the compounds may be volatile enough to be active in the vapour phase against fungi on the plant.

The invention therefore provides a method of combating fungi, which comprises applying to a plant, to a seed of a plant, or to the locus of the plant or seed, a fungicidally effective amount of a compound as hereinbefore defined, or a composition containing the same.

The compounds may also be useful as industrial (as opposed to agricultural) fungicides, e.g. in the prevention of fungal attack on wood, hides, leather and especially paint films.

Some compounds may exhibit plant growth regulating activity and may be deployed for this purpose at appropriate rates of application.

The compounds may be used directly as fungicides but are more conveniently formulated into compositions using a carrier or diluent. The invention thus provides fungicidal compositions comprising a compound as hereinbefore defined, and an acceptable carrier or diluent therefor.

The compounds can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, myclobutanil, propamocarb, R0151297, diniconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole, (2 RS, 3 RS)-2-(4-chlorophenyl)-3-cyclopropyl-1-(1H-1,2,4-triazol-1-yl)butan-2-ol, (RS)-1-(4-chlorophenyl)-4,4-dimethyl-3-(1H-1,2,4-triazol-1-ylmethyl)pentan-3-ol, fluzilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, 4-chloro-N-(cyano(ethoxy)methyl)benzamide, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds. The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout the Examples, the term 'ether' refers to diethyl ether, magnesium sulphate was used to dry solutions, and solutions were concentrated under reduced pressure. Reactions involving water-sensitive intermediates were performed under an atmosphere of nitrogen and solvents were dried before use, where appropriate. Unless otherwise stated, chromatography was performed on a column of silica gel as the stationary phase. Where shown, infrared and NMR data are selective; no attempt is made to list every absorption in all cases. $^1$H NMR spectra were recorded using $CDCl_3$-solutions unless otherwise stated. The following abbreviations are used throughout:

| THF = tetrahydrofuran | s = singlet |
|---|---|
| DMF = N,N-dimethylformamide | d = doublet |
| NMR = nuclear magnetic resonance | t = triplet |
| IR = infrared | m = multiplet |
| m.p. = melting point | br = broad |
| a.i. = active ingredient | RH = relative humidity |
| cv. = cultivar | |
| DMSO = dimethylsulphoxide | GC = Gas Chromatography |

EXAMPLE 1

This Example illustrates the preparation of (E)-methyl 2-[2-(3-chlorophenoxymethyl)phenyl]-3-methoxypropenoate (Compound No. 1 of Table I).

A solution of 3-chlorophenol (9.26 g) in DMF (25 ml) was added dropwise to a stirred suspension of sodium hydride (1.44 g) in DMF (50 ml) (effervescence) and the resulting mixture was stirred at room temperature for 1 hour. A solution of 2-(bromomethyl)benzonitrile (11.76 g) in DMF (25 ml) was then added to the stirred reaction mixture and after a further hour at room temperature the mixture was poured into water and extracted with ether. The extracts were washed successively with water, dilute aqueous sodium hydroxide and brine, then dried and concentrated to give crude 2-(3-chlorophenoxymethyl)benzonitrile (13.95 g) as an orange-brown oil which crystallised on standing. An analytical sample, recrystallised from petrol, had m.p. 56° C.

Raney nickel alloy (9.72 g) was added to a solution of part of the crude (2-(3-chlorophenoxymethyl)benzonitrile (9.72 g) in 75% formic acid (150 ml). The resulting mixture was heated at 150° C. for about 5 hours, further Raney nickel alloy (3 g) was added, and heating at 150° C. was continued for a further 17 hours. The mixture was filtered and the solid was washed with a little methanol. The combined filtrate and washings were diluted with water and extracted with ether. The extracts was washed successively with water, aqueous potassium carbonate and brine, then dried and concentrated to give 2-(3-chlorophenoxymethyl)benzaldehyde (5.80 g) as a yellow-brown oil, ¹H NMR delta 5.51 (2H, s), 10.18 (1H, s) ppm. A mixture of this crude benzaldehyde, methyl(methylthiomethyl)sulphoxide (1.73 g) and Triton B [(40 weight % solution of benzyltrimethylammonium hydroxide in methanol) 1.21 ml] in THF (6 ml) was heated at 110° C. for 3 hours. Further Triton B (2 ml) was added and the mixture was heated for a further 4 hours at 110° C. Further Triton B (2 ml) and methyl (methylthiomethyl)sulphoxide (1.5 ml) were then added and the mixture was heated for a further 6 hours at 110° C. After cooling, the mixture was poured into water and extracted with ether. The extracts were washed with water and brine, dried, concentrated and chromatographed using ether as eluant to give a single stereoisomer of the sulphoxide (A) [1.10 g, 7% yield from 2-(bromomethyl)benzonitrile] as a viscous oil, ¹H NMR delta 2.18 (3H, s), 2.74 (3H, s), 5.04 and 5.12 (each 1H, d J 12 Hz), 7.85 (1H, s) ppm.

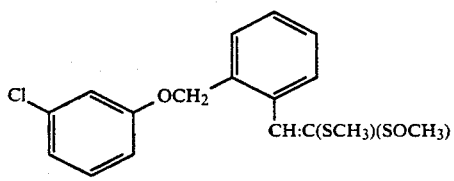

(A)

Hydrogen chloride was bubbled steadily through a stirred solution of the sulphoxide (A) (1.10 g) in dry methanol (50 ml) until the solvent began to boil. The resulting mixture was allowed to cool over 30 minutes, then poured into a mixture of ice and water and extracted with ether. The extracts were washed with water until the washings were neutral, then dried and concentrated to give crude methyl [2-(3-chlorophenoxymethyl)phenyl]acetate (1.03 g) as a yellow oil, ¹H NMR delta 3.67 (3H, s), 3.75 (2H, s), 5.08 (2H, s) ppm. A mixture of this crude acetate (1.03 g) and methyl formate (4.26 ml) in DMF was added dropwise over 10 minutes to a stirred suspension of sodium hydride (0.16 g) in DMF, cooled in ice to below 10° C. (effervescence). Following the addition, the reaction mixture was stirred at room temperature for 30 minutes, then poured into water, acidified with dilute hydrochloric acid, then extracted with ether. The extracts were washed with water, dried and concentrated to give a yellow oil (1.04 g). Potassium carbonate (0.94 g) and dimethyl sulphate (0.40 g) were added successively to a stirred solution of this yellow oil in DMF (12 ml) and the resulting mixture was stirred at room temperature for 17 hours, then poured into water and extracted with ether. The extracts were washed with water, dried, concentrated and chromatographed using a 1:1 mixture of ether and petrol to give the title compound [0.55 g, 53% yield from the sulphoxide (A)] as a colourless solid which recrystallised from petrol to give colourless crystals m.p. 82° C.

¹H NMR : delta 3.71 (3H, s), 3.84 (3H, s), 4.95 (2H, s), 7.59 (1H, s) ppm.

EXAMPLE 2

This Example illustrates the preparation of (E)-methyl 3-methoxy-2-[2-(3-phenoxyphenoxymethyl)-phenyl]propenoate (Compound No. 165 of Table I).

A solution of 3-phenoxyphenol (1.56 g) in DMF (10 ml) was added dropwise to a stirred suspension of sodium hydride (0.34 g) in DMF (5 ml) at room temperature. An hour later, a solution of (E)-methyl 2-[2-(bromomethyl)phenyl]-3-methoxypropenoate (2.0 g, prepared by the method described in EP 0203606, except that benzoyl peroxide was used instead of azodiisobutyronitrile as catalyst in the bromination step) in DMF (10 ml) was added to the reaction mixture, which was then stirred at room temperature for 2 hours. It was poured into water and extracted (×3) with ether. The combined extracts were washed successively with water, aqueous sodium hydroxide (×2) and brine, then dried, concentrated and chromatographed using a 1:1 mixture of ether and petrol as eluant to give the title compound (1.39 g, 51% yield) as an almost colourless oil.

IR (film) : 1711, 1633 cm⁻¹.

¹H NMR : delta 3.66 (3H, s), 3.79 (3H, s), 4.93 (2H, s), 6.52–6.68 (3H, m), 6.95–7.54 (10H, m), 7.56 (1H, s) ppm.

EXAMPLE 3

This Example illustrates the preparation of (E)-methyl 2-[2-(3-formylphenoxymethyl)phenyl]-3-methoxypropenoate (Compound No. 175 of Table I).

Reaction between 3-hydroxybenzaldehyde, sodium hydride and (E)-methyl 2-[2-(bromomethyl)phenyl]-3methoxypropenoate under the conditions described in Example 2, followed by chromatography using a 1:1 mixture of ether and petrol as eluant, gave the title compound in a yield of 66% as an almost colourless oil.

IR (film) : 1703, 1633 cm⁻¹. ¹H NMR : delta 3.72 (3H, s), 3.84 (3H, s), 5.03 (1H, s), 7.16–7.22 (2H, m), 7.30–7.48 (5H, m), 7.51–7.56 (1H, m), 7.61 (1H, s), 9.94 (1H, s) ppm.

EXAMPLE 4

This Example illustrates the preparation of (E)-methyl 2-[2-(3-[hydroxymethyl]phenoxymethyl)-phenyl]-3-methoxypropenoate (Compound No. 178 of Table I).

Sodium borohydride (38mg) was added in portions over 5 minutes to a stirred solution of (E)-methyl 2-[2-(3-formylphenoxymethyl)phenyl]-3-methoxypropenoate (0.325 g, prepared as described in Example 3) at room temperature. After the initial gentle effervescence had subsided, stirring was continued for a further ½ hour, then the 10 mixture was poured into water and extracted (×3) with ether. The ether extracts were combined, washed successively with water and brine, then dried, concentrated and chromatographed using ether as eluant to give the title compound as an oil (0.22 g, 67% yield).

IR (film): 3434, 1708, 1632 cm⁻¹. ¹H NMR: delta 1.79 (1H, t), 3.84 (3H, s), 3.73 (3H, s), 4.64 (2H, d), 4.97 (2H, s), 6.81–6.85 (b 1H, m), 6.90–6.94 (2H, m), 7.16–7.27 (2H, m), 7.30–7.38 (2H, m), 7.54–7.58 (b 1H, m), 7.60 (1H, s) ppm.

EXAMPLE 5

This Example illustrates the preparation of (E)-methyl 2-[2-(3-[phenoxymethyl]phenoxymethyl)-phenyl]-3-methoxy-propenoate (Compound No. 186 of Table I).

A solution of methanesulphonyl chloride (0.56 g) in dichloromethane (1 ml) was added dropwise over 5 minutes to a stirred solution of (E)-methyl 2-[2-(3-[hydroxymethyl]phenoxymethyl)phenyl]-3-methoxy-propenoate (1.07 g, prepared as described in Example 4, except that this material, almost pure, was used without chromatographic purification) and triethylamine (0.56 g) in dichloromethane (15 ml), cooled in an ice-bath (exotherm and white precipitate). After allowing the reaction mixture to warm to room temperature, it was stirred for a further hour. Analysis at this time (by thin-layer and gas chromatography) indicated loss of the starting alcohol. The reaction mixture was poured into water and extracted ($\times 2$) with ether. The combined ether extracts were washed successively with water, dilute hydrochloric acid, water, saturated aqueous sodium bicarbonate solution, water and brine, then dried and concentrated to give a pale yellow oil (1.30 g).

A solution of phenol (0.37 g) in DMF (2 ml) was added dropwise to a stirred suspension of sodium hydride (86 mg) in DMF (7 ml) (effervescence), and the resulting mixture was stirred at room temperature for 2 hours. A solution of the pale yellow oil described above (1.30 g) in DMF (5 ml) was then added dropwise with stirring over 5 minutes, and the resulting mixture was stirred at room temperature for a further hour. It was poured into water and extracted with ether. The ether extracts were combined and washed successively with water, 2M aqueous sodium hydroxide solution, water and brine, then dried, concentrated and chromatographed using a 1:1 mixture of ether and petrol as eluant to give the title compound (0.695 g, 53% yield from the alcohol) as a viscous oil. IR (film): 1709, 1633 cm$^{-1}$. $^1$H NMR: delta 3.69 (3H, s), 3.79 (3H, s), 4.97 (2H, s), 5.02 (2H, s), 6.85 (1H, m), 6.92–7.57 (12H, m), 7.59 (1H, s) ppm.

EXAMPLE 6

This Example illustrates the preparation of (E)-methyl 2-[2-(3-aminophenoxymethyl)phenyl]-3-methoxypropenoate (Compound No. 34 of Table I).

Reaction between 3-aminophenol, sodium hydride and (E)-methyl 2-[2-(bromomethyl)phenyl]-3-methoxypropenoate under the conditions described in Example 2 (except that the reaction mixture was stirred for just 1 hour after addition of the bromo-compound), followed by chromatography using ether as eluant, gave a 27% yield of the title compound as a viscous gum.

IR (film): 3371, 3458, 1703, 1631 cm$^{-1}$.

$^1$H NMR: delta 3.50–3.80 (2H, br s), 3.71 (3H, s), 3.81 (3H, s), 4.92 (2H, s), 6.24–6.60 (3H, m), 7.03 (1H, t), 7.16–7.19 (1H, m), 7.26–7.38 (2H, m), 7.52–7.58 (1H, m), 7.59 (1H, s) ppm.

EXAMPLE 7

This Example illustrates the preparation of (E,E)-methyl 2-[2-(3-[N-benzylidene]aminophenoxymethyl)-phenyl]-3-methoxypropenoate (Compound No. 180 of Table I).

A stirred mixture of (E)-methyl 2-[2-(3-aminophenoxymethyl)phenyl]-3-methoxypropenoate (0.32 g, prepared as described in Example 6) and benzaldehyde (0.13 g) in DMF (5 ml) was heated at 110° C. for 30 hours, then allowed to cool, poured into water and extracted with ether ($\times 3$). The combined extracts were washed successively with water and brine, then dried and concentrated to give an oil. The excess benzaldehyde was removed by bulb-to-bulb distillation at 125° C./0.25 mmHg, to leave, as the residue, the title compound (0.36 g, 86% yield) as a viscous gum.

IR (film): 1708, 1633 cm$^{-1}$.

$^1$H NMR: delta 3.70 (3H, s), 3.80 (3H, s), 5.00 (2H, s), 6.78 (2H, m), 7.16–7.60 (9H, m), 7.59 (1H, s), 7.88 (2H, m), 8.43 (1H, s) ppm.

EXAMPLE 8

This Example illustrates the preparation of (E)-methyl 2-[2-(3-hydroxyphenoxymethyl)phenyl]-3-methoxypropenoate (Compound No. 171 of Table I).

A solution of resorcinol (1.54 g) in DMF (10 ml) was added dropwise to a stirred suspension of sodium hydride (0.05 g) in DMF (5 ml) at room temperature. An hour later, a solution of (E)-methyl 2-[2-(bromomethyl)-phenyl]-3-methoxypropenoate (1.0 g) in DMF (10 ml) was added to the reaction mixture, which was then stirred at room temperature for 4 hours and at 70° C. for 5 hours. After cooling, the mixture was poured into water, acidified with hydrochloric acid, and extracted with ether. The combined extracts were washed thoroughly with water, dried, concentrated and chromatographed using a 1:1 mixture of ether and petrol as eluant to give an oil (0.6 g). Final purification was accomplished by dissolving this oil in ether, extracting the resulting solution with aqueous sodium hydroxide, acidifying these aqueous extracts and re-extracting with ether. This final ether extract was dried and concentrated to give the title compound (0.24 g) as a colourless oil.

$^1$H NMR: delta 3.72 (3H, s), 3.83 (3H, s), 4.94 (2H, s), 5.02 (1H, br s), 6.37–6.53 (3H, m), 7.04–7.56 (5H, m), 7.60 (1H, s) ppm.

EXAMPLE 9

This Example illustrates the preparation of (E)-methyl 3-methoxy-2-[2-(3-[pyrimidin-2-yloxy]phenoxymethyl)phenyl]propenoate (Compound No. 214 of Table I).

A solution of (E)-methyl 2-[2-(3-hydroxyphenoxymethyl)phenyl]-3-methoxypropenoate (0.5 g, prepared as described in Example 8) in DMF (5 ml) was added dropwise to a stirred suspension of sodium hydride (0.03 g) in DMF (5 ml) at room temperature. An hour later, a solution of 2-chloropyrimidine (0.15 g) in DMF (5 ml) was added, and the resulting mixture was heated at 80° C. for 10 hours, then allowed to cool. The mixture was poured into water and extracted with ether. The extracts were washed successively with water ($\times 2$), aqueous sodium hydroxide ($\times 2$) and brine ($\times 1$), then dried and concentrated to give an off-white solid (0.085 g). Trituration of this solid with ether gave the title compound (0.076 g) as a white solid, m.p. 157°–165° C.

$^1$H NMR: delta 3.68 (3H, s), 3.80 (3H, s), 4.96 (2H, s), 6.76–6.87 (3H, m), 7.04 (1H, t), 7.17 (1H, m), 7.26–7.40 (3H, m), 7.56 (1H, m), 7.58 (1H, s), 8.57 (2H, d) ppm.

EXAMPLE 10

This Example illustrates the preparation of (E)-methyl 2-[2-(pyridin-2-yloxymethyl)phenyl]-3-methoxypropenoate (Compound No. 67 of Table I).

A mixture of 2-hydroxypyridine (0.50 g) and (E)-methyl 2-[2-(bromomethyl)phenyl]-3-methoxypropenoate (2.25 g) was suspended in dry n-hexane (10 ml) and silver carbonate (0.73 g) was added. The mixture was stirred and heated under reflux for 2 hours in the dark. The cooled mixture was then concentrated and the residue was extracted with dichloromethane. The extracts were filtered through Hyflosupercel, washed successively with saturated aqueous sodium bicarbonate solution and water, then dried, concentrated and chromatographed using a 2:1 mixture of ether and petrol to give the title compound as a colourless oil which crystallised on standing (0.80 g, 51% yield from 2-hydroxypyridine). Recrystallisation from petrol gave a white powder, m.p. 65°–66° C.

$^1$H NMR (400 MHz): delta 3.68 (3H, s), 3.80 (3H, s), 5.26 (2H, s), 6.74 (1H, d), 6.82–6.90 (1H, m), 7.14–7.21 (1H, m), 7.28–7.42 (2H, m), 7.49–7.63 (2H, m), 7.54 (1H, s), 8.15 (1H, d) ppm.

EXAMPLE 11

This Example illustrates the preparation of (E)-methyl 2-[2-(2,3-difluorophenoxymethyl)phenyl]-3-methoxypropenoate (Compound No. 41 of Table I).

Lithium chloride (4.0 g) was stirred with N-methyl-2-pyrrolidinone (25 ml) at 50° C. After 40 minutes, (E)-methyl 2-[2-(bromomethyl)phenyl]-3-methoxypropenoate (2.0 g) was added and the mixture was stirred for 1 hour at 50° C. The reaction mixture was cooled and poured into water (100 ml) and then extracted with ether (2×75 ml). The combined extracts were washed with brine (2×75 ml). dried and evaporated to give a white solid (1.66 g), which was recrystallised from petrol (60°–80° C.) to give (E)-methyl 2-[2-(chloromethyl)phenyl]-3-methoxypropenoate (1.0 g, 59% yield) as a white crystalline solid melting at 89°–91° C.- A mixed m.p. with (E)-methyl 2-[2-(bromomethyl)phenyl]-3-methoxypropenoate (m.p. 88°–90° C.) gave a depressed m.p. of 85°–88° C.

IR (nujol): 1706, 1628 cm$^{-1}$.

$^1$H NMR (CDCl$_3$): delta 3.70 (3H, s), 3.83 (3H, s), 4.50 (2H, s), 7.1–7.6 (4H, m), 7.64 (1H, s) ppm.

A solution of 2,3-difluorophenol (0.25 g) in DMF (3 ml) was added dropwise to a stirred suspension of sodium hydride (0.0385 g) in DMF (7 ml) at room temperature. An hour later, a solution of (E)-methyl 2-[2-chloromethyl) phenyl]-3-methoxypropenoate (0.385 g) in DMF (5 ml) was added and the mixture was stirred for 16 hours at room temperature, and then warmed to 50° C. for 4 hours. The reaction mixture was poured into water (100 ml) and extracted with ether (2×75 ml). The ether extracts were washed with brine, dried and evaporated to give a clear oil. Purification by chromatography using a 7:3 mixture of ether and petrol (60°–80° C.) as eluant gave the title compound (123 mg, 23% yield) as a white crystalline solid melting at 60°–62° C.

IR (film): 1709, 1632 cm$^{-1}$.

$^1$H NMR (CDCl$_3$): delta 3.70 (3H, s), 3.83 (3H, s), 5.04 (2H, s), 6.6–7.0 (3H, m), 7.1–7.6 (4H, m), 7.60 (1H, s) ppm.

EXAMPLE 12

This Example illustrates the preparation of methyl 2-(2-chlorophenoxymethyl)phenylacetate, an intermediate for the preparation of (E)-methyl 2-[2-(2-chlorophenoxymethyl)phenyl]-3-methoxypropenoate (Compound No. 157 of Table I).

2-Chlorophenol (1.30 g) was added to a solution of potassium hydroxide (0.38 g) in a little water, and the resulting mixture was stirred for an hour at room temperature and 15 minutes at 50° C. 3-Isochromanone (1.0 g) was added to the reaction mixture and it was heated in an open-topped flask at 150° C. for 5 hours. A further 1.3 g of 2-chlorophenol was then added, an air condenser was fitted to the flask, and heating at 150° C. was continued for a further 6 hours. After cooling, the reaction mixture, a viscous brown oil, was dissolved in a mixture of ethyl acetate and dilute hydrochloric acid. The organic and aqueous layers were separated and the latter was extracted (×3) with further ethyl acetate. The combined ethyl acetate layers were washed with water (×3), dried and concentrated to give a viscous brown oil (2.76 g). This oil was dissolved in methanol (60 ml), a few drops of concentrated hydrochloric acid were added, and the solution was heated under reflux for 6 hours. After cooling, the mixture was poured into water and extracted (×3) with ether. The extracts were washed successively with water, aqueous sodium hydroxide and brine, then dried and concentrated to give methyl 2-(2-chlorophenoxymethyl)phenylacetate (0.36 g) as an oil.

IR (film): 1733 cm$^{-1}$.

$^1$H NMR: delta 3.67 (3H, s), 3.80 (2H, s), 5.19 (2H, s). 6.86–7.53 (8H, m) ppm.

EXAMPLE 13

This Example illustrates the preparation of (E)-methyl 3-methoxy-2-[2-(N-methyl-N-phenyl-aminomethyl)phenyl]propenoate (Compound No. 2 of Table III).

A mixture of (E)-methyl 2-[2-(bromomethyl)phenyl]-3-methoxypropenoate (10.0 g, 90% pure), sodium hydrogen orthophosphate dibasic (Na$_2$HPO$_4$, 5.74 g) and potassium hydrogen monophosphate monobasic (KH$_2$PO$_4$.0.55 g) in DMSO (20 ml) was heated at 80° C. for 1 hour and then at 110° C. for a further hour (compare J H Babler, M J Coghlan, M Feng and P Fries, *J.Org.Chem.*, 1979, 44, 1716). After cooling, the reaction mixture was poured into water and extracted with ether. The extracts were washed with brine, dried, concentrated and chromatographed using ether as eluant to give (E)-methyl 2-(2-formylphenyl)-3-methoxypropenoate (2.77 g, 40% yield) as a white crystalline solid, m.p. 67°–69° C.

IR (nujol): 1710, 1634 cm$^{-1}$.

$^1$H NMR: delta 3.72 (3H, s), 3.84 (3H, s), 7.30–7.65 (3H, m), 7.69 (1H, s), 7.9 (1H, m), 10.0 (1H, s) ppm.

A mixture of (E)-methyl 2-(2-formylphenyl)-3-methoxypropenoate (0.10 g), N-methylaniline (0.27 g) and glacial acetic acid (1 ml) in 40°–60° C. petrol (ca. 3 ml) was stirred at room temperature. After 2 hours, boranepyridine complex (0.4 ml) was added, and the resulting mixture was stirred for a further 2 hours. 5M Hydrochloric acid (2 ml) was added followed, when evolution of gas was complete, by aqueous sodium hydroxide until the mixture was basic. The mixture was extracted with ether. The extracts were washed with brine, dried, concentrated and chromatographed using a 1:1 mixture of petrol and ether as eluant to give the title compound (0.08 g) as a white crystalline solid, m.p. 115°-121° C., which turned mauve on standing.

$^1$H NMR: delta 3.01 (3H, s), 3.72 (3H, s), 3.86 (3H, s), 4.35 (2H, s), 7.54 (1H, s) ppm.

EXAMPLE 14

This Example illustrates an alternative preparation of (E)-methyl 2-[2-(bromomethyl)phenyl]-3-methoxypropenoate.

Bromine (0.25 ml) was added to a stirred solution of (E)-methyl 3-methoxy-2-(2-methylphenyl)propenoate (1.0 g) and azodiisobutyronitrile (0.1 g) in chloroform (40 ml) at room temperature, with illumination from a 100 watt tungsten lamp. After 3 hours the reaction mixture was poured into sodium metabisulphite (50 ml of a 50% aqueous solution). The organic phase was separated and washed with water, then dried and concentrated to give a clear oil (1.2 g). Purification by chromatography using silica gel with ether and hexane (1:1) as the eluant gave the title compound (240 mgs, 17% yield) melting at 88°-90° C. A mixed melting point with material prepared as described in Example 2 indicated no depression in the melting point.

IR (nujol mull): 1704, 1627 cm$^{-1}$.

$^1$H NMR (270 MHz), delta: 3.70 (3H, s), 3.83 (3H, s), 4.41 (2H, s), 7.1-7.6 (4H, m), 7.64 (1H, s) ppm.

EXAMPLE 15

This Example illustrates the preparation of (E)-methyl 2-[2-(1-[3-chlorophenoxy]ethy)phenyl]-3-methoxypropenoate (Compound No. 3 of Table I).

Methyl 2-ethylbenzoate was prepared in a yield of 92% by heating a solution of the corresponding acid in acidic methanol.

N-Bromosuccinimide (10.7 g) and azodiisobutyronitrile (catalytic) were added to a solution of methyl 2-ethylbenzoate (10 g) in carbon tetrachloride (50 ml), and the resulting mixture was heated at 80° C. for 6 hours under reflux. After cooling, the reaction mixture was filtered and the filtrate was concentrated to give methyl 2-(1-bromoethyl)benzoate (12 g), almost pure by GC and NMR, as a yellow oil.

$^1$H NMR (400 MHz): delta 2.05 (3H, d), 3.94 (3H, s), 6.31 (1H, q), 7.33 (1H, t), 7.55 (1H, t), 7.83 (2H, apparent t) ppm.

A solution of 3-chlorophenol (8.2 g) in DMF (30 ml) was added dropwise to a stirred suspension of sodium hydride (1.3 g) in DMF (30 ml). An hour later, a solution of crude methyl 2-(1-bromoethyl)benzoate described above (12 g) in DMF was added with stirring. After stirring at room temperature for 2 hours, the resulting mixture was poured into water and extracted with ether. The ether extracts were washed successively with water (×2), aqueous sodium hydroxide (×2), and brine, then dried and concentrated to give methyl 2-[1-(3-chlorophenoxy)ethyl]benzoate (14.84 g, 88% pure by GC), as a yellow oil.

$^1$H NMR (270 MHz): delta 1.62 (3H, d), 3.95 (3H, s), 6.28 (1H, q), 6.67 (1H, dd), 6.84 (2H, m), 7.06 (1H, t), 7.30 (1H, t), 7.47 (1H, t), 7.63 (1H, d), 7.96 (1H, d) ppm.

A solution of the crude methyl 2-[1-(3-chlorophenoxy)ethyl]benzoate described above (14.8 g) in THF (50 ml) was added dropwise to a stirred suspension of lithium aluminium hydride (1.93 g) in THF (70 ml) cooled to 0°-5° C. Following the addition, the reaction mixture was stirred at about 0° C. for 30 minutes, then at room temperature for 2 hours. It was poured carefully into water and was extracted with ether. The extracts were washed successively with water (×2) and brine, then dried and concentrated to give 2-[1-(3-chlorophenoxy)ethyl]benzyl alcohol (11.72 g, 85% pure by GC) as a yellow oil.

$^1$H NMR (400 MHz): delta 1.66 (3H, d), 4.76 (1H, d), 4.85 (1H, d), 5.68 (1H, q) ppm.

Manganese dioxide (6.65 g) was added to a solution of part of the crude benzyl alcohol described above (4.02 g) in dichloromethane (100 ml) and the resulting mixture was heated at 40° C. under reflux for 24 hours. The mixture was filtered, and the filtrate was concentrated to give 2-[1-(3-chlorophenoxy)ethyl]benzaldehyde (3.53 g) containing (by GC analysis) 30% of the benzyl alcohol starting material.

IR (film): 1691 cm$^{-1}$.

The crude benzaldehyde was converted into methyl 2-[1-(3-chlorophenoxy)ethyl]phenylacetate by the 2 steps described in Example 1 for a similar conversion, that is by condensation with methyl(methylthiomethyl)sulphoxide in the presence of Triton B, followed by acidic methanolysis of the resulting sulphoxide. The phenylacetate, an oil, was purified by chromatography using a mixture of hexane and ether (7:3) as eluant.

IR (film): 1739 cm$^{-1}$.

$^1$H NMR (270 MHz) delta: 1.61 (3H, d, J 6.5 Hz), 3.70 (3H, s), 3.74 (2H, s), 5.49 (1H, q, J 6.5 Hz), 6.71 (1H, dd), 6.85 (2H, m), 7.10 (1H, t, J 8 Hz), 7.26 (3H, m), 7.44 (1H, m) ppm.

The phenylacetate was converted into the title compound by the 2 steps described for a similar conversion in Example 1, that is by treatment with methyl formate and sodium hydride, and then with dimethyl sulphate and potassium carbonate. The title compound, an oil, was purified by chromatography using a mixture of ether and hexane (1:1) as eluant.

IR (film): 1712, 1634 cm$^{-1}$.

$^1$H NMR (270 MHz): delta 1.50 (3H, d, J 7 Hz), 3.72 (3H, br s), 3.87 (3H, br s), 5.19 (1H, br q, J 7 Hz), 6.8 (2H, m), 7.1 (2H, m), 7.3 (3H, m), 7.42 (1H, m), 7.63 (1H, s) ppm.

The following Examples of compositions suitable for agricultural and horticultural purposes which can be formulated from the compounds of the invention. Such compositions from another aspect of the invention. Percentages are by weight.

EXAMPLE 16

An emulsifiable concentrate is made up by mixing and stirring the ingredients until all are dissolved.

| | |
|---|---|
| Compound No. 1 of Table I | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 17

The active ingredient is dissolved in methylene dichloride and the resultant liquid sprayed on to the granules of attapulgite clay. The solvent is then allowed to evaporate to produce a granular composition.

| | |
|---|---|
| Compound No. 1 of Table I | 5% |

| | |
|---|---|
| Attapulgite granules | 95% |

EXAMPLE 18

A composition suitable for use as a seed dressing is prepared by grinding and mixing the three ingredients.

| | |
|---|---|
| Compound No. 1 of Table I | 50% |
| Mineral oil | 2% |
| China clay | 48% |

EXAMPLE 19

A dustable powder is prepared by grinding and mixing the active ingredient with talc.

| | |
|---|---|
| Compound No. 1 of Table I | 5% |
| Talc | 95% |

EXAMPLE 20

A suspension concentrate is prepared by ball milling the ingredients to form an aqueous suspension of the ground mixture with water.

| | |
|---|---|
| Compound No. 1 of Table I | 40% |
| Sodium lignosulphonate | 10% |
| Bentonite clay | 1% |
| Water | 49% |

This formulation can be used as a spray by diluting into water or applied directly to seed.

EXAMPLE 21

A wettable powder formulation is made by mixing together and grinding the ingredients until all are thoroughly mixed.

| | |
|---|---|
| Compound No. 1 of Table I | 25% |
| Sodium lauryl sulphate | 2% |
| Sodium lignosulphonate | 5% |
| Silica | 25% |
| China clay | 43% |

EXAMPLE 22

Compounds of the invention were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration with water immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace–5% of disease on untreated plants
2 = 6–25% of disease on untreated plants
1 = 26–59% of disease on untreated plants
0 = 60–100% of disease on untreated plants The results are shown in Table V.

TABLE V

| COMPOUND NO. | TABLE NO. | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|---|
| 1 | I | 4 | 4 | 4 | 4 | 4 | 4 | 4 |
| 23 | I | 4 | 4 | 4 | 4 | 4 | 4 | 4 |
| 24 | I | 4 | 4 | 4 | 4 | 4 | 4 | 4 |
| 25 | I | 4 | 4 | 4 | 2 | 4 | 4 | 3 |
| 27 | I | 4 | 4 | 4 | 1 | 4 | 0 | 4 |
| 29 | I | 4 | 2 | 4 | 4 | 4 | 4 | 4 |
| 33 | I | 4 | 2 | 4 | 4 | 4 | 4 | 3 |
| 34 | I | 3 | 0 | 3 | 0 | 0 | 4 | 4 |
| 38 | I | 4 | 4 | 4 | 0 | 4 | 4 | 4 |
| 43 | I | 4 | 4 | 4 | 4 | 4 | 4 | 4 |
| 44 | I | 4 | 4 | 4 | 2 | 3 | 4 | 3 |
| 45 | I | 4 | 3 | 4 | 4 | 4 | 4 | 4 |
| 67 | I | 4 | 4 | 4 | 4 | 4 | 4 | 4 |
| 68 | I | 3 | 4 | 4 | 3 | 3 | 4 | 3 |
| 149 | I | 4 | 4 | 4 | 4 | — | 4 | 4 |
| 155 | I | 4 | 4 | 4 | 4 | 4 | 4 | 4 |
| 156 | I | 4 | 4 | 4 | 0 | 4 | 4 | 4 |
| 157 | I | 4 | 4 | 4 | 4 | 4 | 4 | 3 |
| 158 | I | 4 | 4 | 4 | 4 | 4 | 4 | 3 |
| 159 | I | 4 | 3 | 4 | 0 | 4 | 0 | 3 |
| 160 | I | 4 | 4 | 4 | 3 | 3 | 4 | 4 |

TABLE V-continued

| COMPOUND NO. | TABLE NO. | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|---|
| 161 | I | 3 | 3 | 4 | 0 | 3 | 4 | 1 |
| 162 | I | 4 | 4 | 4 | 2 | 4 | 4 | 3 |
| 163 | I | 4 | 4 | 4 | 2 | 4 | 4 | 4 |
| 164 | I | 4 | 4 | 4 | 4 | 4 | 4 | 3 |
| 165 | I | 4 | 4 | 0 | 4 | 0 | 4 | 4 |
| 166 | I | 4 | 4 | 4 | 4 | 4 | 4 | 4 |
| 167 | I | 4 | 4 | 4 | 4 | 3 | 4 | 4 |
| 168 | I | 4 | 4 | 4 | 4 | 3 | 4 | 4 |
| 169 | I | 3 | 1 | 4 | 0 | 4 | 4 | 4 |
| 170 | I | 0 | 4 | 4 | 3 | 4 | 4 | 4 |
| 171 | I | 3 | 1 | 4 | 0 | 3 | 4 | 3 |
| 172 | I | 4 | 4 | 4 | 0 | 4 | 4 | 4 |
| 173 | I | 4 | 3 | 4 | 0 | 4 | 4 | 4 |
| 174 | I | 4 | 4 | 4 | 0 | 4 | 4 | 4 |
| 175 | I | 3 | 1 | 4 | 0 | 1 | 4 | 4 |
| 176 | I | 4 | 4 | 4 | 4 | — | 4 | 4 |
| 177 | I | 4 | 4 | 4 | 4 | — | 4 | 4 |
| 178 | I | 3 | 0 | 0 | 2 | 3 | 4 | 2 |
| 179 | I | 3 | 0 | 0 | 2 | 0 | 4 | 4 |
| 180 | I | 3 | 0 | 0 | 2 | 4 | 4 | 4 |
| 181 | I | 4 | 4 | 4 | 3 | 4 | 4 | 4 |
| 182 | I | 4 | 4 | 3 | 4 | 4 | 4 | 4 |
| 183 | I | 0 | 4 | 4 | 3 | 4 | 4 | 4 |
| 184 | I | 4 | 4 | 4 | 3 | 4 | 4 | 4 |
| 185 | I | 4 | 4 | 2 | 4 | 4 | 4 | 4 |
| 1 | II | 4 | 2 | 4 | 3 | 0 | 4 | 4 |
| 4 | III | 0* | 0* | 3* | 0* | 0* | 1* | 0* |
| 2 | II | 4 | 4 | 4 | 4 | 0 | 4 | 4 |

*=25 ppm foliar spray only.

EXAMPLE 23

Compounds 1 and 23 of Table I were tested for phytotoxicity on peanut and tomato plants and Compound No. of Table I was tested for phytotoxicity on tomato alone. For comparative purposes only, the known compound (E)-methyl 2-(2-phenoxymethyl)phenyl-3-methoxypropenoate (disclosed in EP-A-0178826 and forming no part of the present invention) was tested side-by-side in the same way. This compound is referred to hereafter as the "comparative compound."

The testing procedure was as follows.

(a) Peanut

Peanut plants, cv. Tomnut, were propagated in John Innes No. 1 compost. They were grown under controlled environmental conditions i.e. a 16 hour light and 8 hour dark regime of 27° C./80% RH and 20° C./95% RH respectively. Uniform, 8–10 day-old plants were selected for the experiments.

The test compounds were formulated in 5 cm³ DISPERSOL T*, diluted to the desired concentration with deionised water, and applied to the plants as root drenches (10 mls per treatment).

* A mixture of sodium sulphate and a condensate of formaldehyde with sodium naphthalene sulphone. DISPERSOL T is a Registered Trademark, the property of Imperial Chemical Industries PLC.

All treatments were replicated four times. Control plants were treated with a root drench of deionised water. All plants were maintained at approximately 27° C. under glasshouse conditions.

One week after treatment plants were assessed for phytotoxicity, by comparison with the controls. Phytotoxicity was assessed on a linear 0–5 scale where grade 1=slight damage and grade 5=dead plant. The results are displayed in Table VI.

(b) Tomato

Tomato plants, cv. Outdoor Girl, grown in John Innes No. 1 compost, were selected for uniformity after 20 days growth under glasshouse conditions at 24° C.

The test compound was formulated in 5 cm³ DISPERSOL T and diluted to the desired concentration with deionised water. All plant surfaces were sprayed to maximum retention using a hand held Devilbiss spray gun at 10 psi. Following chemical treatment plants were maintained under a 16 hour light and 8 hour dark regime at 21° C./60% RH and 18° C./95% RH respectively. All treatments were replicated four times. Control plants were sprayed with deionised water.

One week after treatment plants were assessed for phytotoxicity in a similar manner to that previously described for peanuts.

In tests including Compound No. 169, of Table I treatments were applied 3 times at 3–4 day intervals and phytotoxicity assessments undertaken one week after the final application.

TABLE VI

| | (a) Tomato | | | (b) Peanut |
|---|---|---|---|---|
| COMPOUND TESTED | 300 | 100 | 30 (ppm) | 100 (ppm) |
| Compound 1, Table I | 1.5 | 0.63 | 0.75 | 0 |
| Compound 23, Table I | 2.3 | 1.5 | 0.3 | 0.13 |
| Comparative Compound | 3.0 | 3.4 | 2.8 | 1.5 |

TABLE VII

| | Tomato | | |
|---|---|---|---|
| COMPOUND TESTED | 100 | 30 | 10 (ppm) |
| Compound 169, Table I | 1.5 | 0.9 | 0.3 |
| Comparative Compound | 3.4 | 3.4 | 2.8 |

Conclusions

The results displayed in Tables VI and VII show that the compounds of the invention Nos. 1, 23 and 169 of Table I (substituted with chlorine or diethylamino in the phenyl ring of the phenoxymethyl moiety) are less phytotoxic than the corresponding unsubstituted comparative compound.

EXAMPLE 24

This Example illustrates the plant growth regulating properties of compounds 1, 23 and 68 of Table I when tested on a whole plant screen against various species of plant. The plant species are identified in Table VII with the leaf stage at which they are sprayed.

A formulation of each chemical was applied at 4000 ppm (4 kg/ha in a 1000 l/ha field volume) using a track-sprayer and a SS8004E (Teejet) nozzle.

After spraying the plants were grown in a glasshouse with 25° C. day/22° C. night temperature. Supplementary lighting was supplied when necessary to provide an average photoperiod of 16 hours (14 hours minimum).

After 2-6 weeks in the glasshouse, depending on species and time of year, the plants were visually assessed for morphological characteristics against a control of plant sprayed with a blank formulation. The results are presented in Table VIII.

TABLE VII

PLANT MATERIAL USED FOR WHOLE PLANT SCREEN

| SPECIES | CODE | VARIETY | GROWTH STAGE AT TREATMENT | NO. PLANTS PER 3" POT | COMPOST TYPE |
|---------|------|---------|---------------------------|----------------------|--------------|
| Maize | MZ | Earliking | 2¼-2½ leaves | 1 | PEAT |
| Barley | BR | Atem | 1-1.5 leaves | 4 | JIP* |
| Tomato | TO | Ailsa Craig | 2-2½ leaves | 1 | PEAT |

*John Innes Potting Compost

TABLE VIII

| PLANT MATERIAL | COMPOUND NO. (TABLE I) | R | G | A | T | I | P |
|----------------|------------------------|---|---|---|---|---|---|
| TO | 1 | 3 | | 3 | 1 | | 2 |
| TO | 23 | 3 | | 3 | | | 3 |
| TO | 68 | | | | | | |
| BR | 68 | | | | 1 | | |
| MZ | 1 | 1 | 1 | | | 1 | |
| MZ | 23 | | | | | | |

Key:
R = Retardation
G = Greening effect
A = Apical damage
T = Tillering or side shooting
I = Interligular or internodal length reduction
P = Phytotoxicity
All effects, except phytotoxicity, are scored visually on a 1-3 basis where
1 = 10-30%
2 = 31-60%
3 = 61-100%
Blank means less than 10% effect.
Phytotoxicity is scored on a 1-5 basis where
1 = less than 10%
2 = 11-30%
3 = 31-50%
4 = 51-70%
5 = greater than 70%
Blank means no effect at all observed.

We claim:
1. A compound of the formula (I):

$$\text{(I)}$$

and stereoisomers thereof, wherein $R^1$ is optionally substituted heteroaryl; Y is oxygen, sulphur or $NR^4$; $R^2$, $R^3$ and $R^4$, which may be the same or different, are hydrogen, $C_{1-4}$ alkyl or $C_{2-4}$ alkenyl; X is halogen, $C_{1-4}$ alkyl, $C_{2-4}$ alkenyl, $C_{1-4}$ alkoxy, nitro or cyano; and n is 0 or an integer of 1 to 4.

2. A compound according to claim 1 of the formula (Ic):

$$\text{(Ic)}$$

in which B is N or CH; Y is oxygen, sulphur or $NR^4$ where $R^4$ is hydrogen, $C_{1-4}$ alkyl or $C_{2-4}$ alkenyl; p is 0 or an integer of 1 to 3 when B is N, or 0 or an integer of 1 to 4 when B is CH; and $A^1$ is halo, hydroxy, $C_{1-4}$ alkyl, halo($C_{1-4}$)alkyl, $C_{1-4}$ alkoxy, halo($C_{1-4}$)alkoxy, phenyl, phenoxy, nitro, amino, acylamino, cyano, carboxy, $C_{1-4}$ alkoxycarbonyl or $C_{1-4}$ alkylcarbonyloxy.

3. A compound according to claim 2 in which Y is attached to a position ortho ring nitrogen atom, or a substituent $A^1$ is attached to a position ortho to a ring nitrogen atom, or both.

4. A compound according to claim 1 wherein Y is oxygen and $R^2$ and $R^3$ are hydrogen.

5. A compound according to claim 1 in which Y is $NR^4$ and $R^1$ is substituted with an electron withdrawing group.

6. A process for preparing a compound according to claim 1 which comprises
(a) treating a compound of formula (II):

$$\text{(II)}$$

with a compound of the formula $CH_3L$; or
(b) eliminating the elements of methanol from a compound of formula (IV):

$$\text{(IV)}$$

under acidic or basic conditions; or
(c) treating a ketoester of formula (VI):

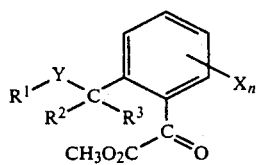

with methoxymethylenating reagent; or (d) treating a compound of formula (X):

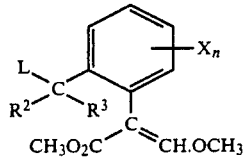

with a compound of formula $R^1YM$; or (e) treating a compound of formula (XIII):

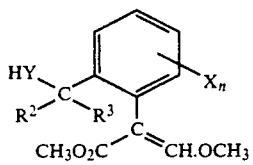

with a compound $R^1L$ in the presence of a base; or (f) when Y is $NR^4$ reducing an amide of formula (XVIII):

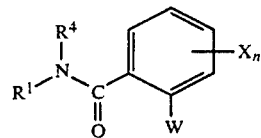

or treating a carbonyl compound of formula (XVII):

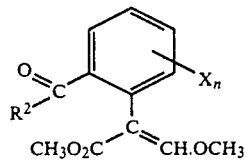

with a primary or secondary amine of formula $R^1R^4NH$ and a suitable reducing agent, in which $R^1$, $R^2$, $R^3$, $R^4$, Y, X and n have the meanings given in claim 1, $R^5$ and M are metal atoms, L is a leaving group and W is a group which may be converted into the group $CH_3O.OCH:C(CO_2CH_3)$.

7. A fungicidal composition comprising a fungicidally effective amount of a compound according to claim 1.

8. A method of combating fungi which comprises applying to plants, to the seeds of plants or to the locus of the plants or seeds, a compound according to claim 1.

9. A compound according to claim 1 wherein $R^1$ is pyridin-2-yl, Y is O and $R^2$, $R^3$ and X are hydrogen.

* * * * *